(12) United States Patent
Badylak et al.

(10) Patent No.: US 12,201,745 B2
(45) Date of Patent: Jan. 21, 2025

(54) VASCULAR EXTRACELLULAR MATRIX HYDROGEL

(71) Applicant: University of Pittsburgh—Of the Commonwealth System of Higher Education, Pittsburgh, PA (US)

(72) Inventors: Stephen F. Badylak, West Lafayette, IN (US); Julie Anne Phillippi, Pittsburgh, PA (US); Thomas G. Gleason, Pittsburgh, PA (US); George R. Fercana, Jr., Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 237 days.

(21) Appl. No.: 17/808,423

(22) Filed: Jun. 23, 2022

(65) Prior Publication Data
US 2022/0323646 A1    Oct. 13, 2022

Related U.S. Application Data

(62) Division of application No. 16/070,044, filed as application No. PCT/US2017/013355 on Jan. 13, 2017, now Pat. No. 11,406,736.

(60) Provisional application No. 62/278,065, filed on Jan. 13, 2016.

(51) Int. Cl.
| | | |
|---|---|---|
| A61L 27/36 | (2006.01) | |
| A61K 35/12 | (2015.01) | |
| A61L 27/22 | (2006.01) | |
| A61L 27/50 | (2006.01) | |
| A61L 27/52 | (2006.01) | |
| C07K 14/745 | (2006.01) | |
| C07K 14/75 | (2006.01) | |

(52) U.S. Cl.
CPC .......... *A61L 27/3625* (2013.01); *A61K 35/12* (2013.01); *A61L 27/225* (2013.01); *A61L 27/3633* (2013.01); *A61L 27/3687* (2013.01); *A61L 27/3691* (2013.01); *A61L 27/507* (2013.01); *A61L 27/52* (2013.01); *C07K 14/745* (2013.01); *C07K 14/75* (2013.01); *A61L 2430/20* (2013.01); *C12N 2533/90* (2013.01)

(58) Field of Classification Search
CPC ............. A61L 27/3625; A61L 27/3633; A61L 27/3687; A61L 27/507; A61L 27/52
See application file for complete search history.

(56) References Cited

U.S. PATENT DOCUMENTS

| | | |
|---|---|---|
| 5,258,042 A | 11/1993 | Mehta |
| 5,730,757 A | 3/1998 | Benetti et al. |
| 5,913,876 A | 6/1999 | Taylor et al. |
| 5,925,054 A | 7/1999 | Taylor et al. |
| 6,001,111 A | 12/1999 | Sepetka et al. |
| 6,171,610 B1 | 1/2001 | Vacanti et al. |
| 6,214,022 B1 | 4/2001 | Taylor et al. |
| 6,308,104 B1 | 10/2001 | Taylor et al. |
| 6,381,499 B1 | 4/2002 | Taylor et al. |
| 6,602,189 B1 | 8/2003 | Bennetti et al. |
| 6,926,662 B1 | 8/2005 | Aboul-Hosn et al. |
| 7,780,725 B2 | 8/2010 | Huang et al. |
| 7,780,950 B2 | 8/2010 | Hazen |
| 7,785,246 B2 | 8/2010 | Aboul-Hosn et al. |
| 7,790,141 B2 | 9/2010 | Pathak et al. |
| 7,795,218 B2 | 9/2010 | McKerracher et al. |
| 7,795,221 B2 | 9/2010 | Sharma et al. |
| 7,795,242 B2 | 9/2010 | Van Rhijn et al. |
| 7,799,070 B2 | 9/2010 | Bates et al. |
| 7,803,178 B2 | 9/2010 | Whirley et al. |
| 7,803,374 B2 | 9/2010 | Lanza et al. |
| 7,806,857 B2 | 10/2010 | Khosravi et al. |
| 7,811,622 B2 | 10/2010 | Bates et al. |
| 7,815,661 B2 | 10/2010 | Mirizzi et al. |
| 7,815,946 B1 | 10/2010 | Murthy et al. |
| 7,816,369 B2 | 10/2010 | Guicherit et al. |
| 7,818,084 B2 | 10/2010 | Boyden et al. |
| 7,820,193 B2 | 10/2010 | Hunter et al. |
| 7,824,698 B2 | 11/2010 | Potts et al. |
| 7,828,840 B2 | 11/2010 | Biggs et al. |
| 7,833,148 B2 | 11/2010 | Noishiki |
| 7,833,978 B2 | 11/2010 | Chaikof et al. |
| 7,837,669 B2 | 11/2010 | Dann et al. |
| 7,837,726 B2 | 11/2010 | Von Oepen et al. |
| 7,840,263 B2 | 11/2010 | Girouard et al. |
| 7,846,138 B2 | 12/2010 | Dann et al. |
| 7,846,202 B2 | 12/2010 | Bates et al. |
| 7,850,645 B2 | 12/2010 | Atanasoska et al. |
| 7,850,676 B2 | 12/2010 | Wood, Jr. |

(Continued)

FOREIGN PATENT DOCUMENTS

| | | |
|---|---|---|
| CN | 103124570 A | 5/2013 |
| CN | 103536967 A | 1/2014 |

(Continued)

OTHER PUBLICATIONS

Badylak et al., "Small Intestinal Submucosa as a Large Diameter Vascular Graft in the Dog", Journal of Surgical Research, 1989, vol. 47, pp. 74-80.

(Continued)

*Primary Examiner* — Taeyoon Kim
(74) *Attorney, Agent, or Firm* — The Webb Law Firm

(57) ABSTRACT

Provided herein are methods of making an ECM gel from vascular tissue. Also provided herein are ECM compositions prepared from vascular tissue, and methods of use of those compositions, for example in treatment of aneurysms, and for vascularization or re-vascularization.

20 Claims, 17 Drawing Sheets

(56) References Cited

U.S. PATENT DOCUMENTS

| | | |
|---|---|---|
| 7,850,729 B2 | 12/2010 | Melvin |
| 7,851,189 B2 | 12/2010 | Freyman et al. |
| 7,854,743 B2 | 12/2010 | Palasis et al. |
| 7,854,759 B2 | 12/2010 | Shirley |
| 7,854,944 B2 | 12/2010 | Mandrusov et al. |
| 7,858,296 B2 | 12/2010 | Sowemimo-Coker et al. |
| 7,862,605 B2 | 1/2011 | Ragheb et al. |
| 7,867,169 B2 | 1/2011 | Webler et al. |
| 7,867,217 B2 | 1/2011 | Wood, Jr. |
| 7,867,275 B2 | 1/2011 | Bates et al. |
| 7,871,402 B2 | 1/2011 | Wood, Jr. |
| 7,872,068 B2 | 1/2011 | Khosravi et al. |
| 7,875,017 B2 | 1/2011 | Sabbah |
| 7,875,272 B2 | 1/2011 | Messina et al. |
| 7,875,273 B2 | 1/2011 | Messina et al. |
| 7,877,142 B2 | 1/2011 | Moaddeb et al. |
| 7,878,978 B2 | 2/2011 | Conrad et al. |
| 7,879,023 B2 | 2/2011 | Wood, Jr. |
| 7,879,062 B2 | 2/2011 | Galdonik et al. |
| 7,879,067 B2 | 2/2011 | Galdonik et al. |
| 7,879,576 B2 | 2/2011 | Fenical et al. |
| 7,892,214 B2 | 2/2011 | Kagan et al. |
| 7,892,246 B2 | 2/2011 | Akin et al. |
| 8,257,434 B2 | 9/2012 | Matheny |
| 8,409,275 B2 | 4/2013 | Matheny |
| 8,449,607 B2 | 5/2013 | Matheny |
| 8,465,771 B2 | 6/2013 | Wan et al. |
| 8,535,719 B2 | 9/2013 | Badylak et al. |
| 8,540,615 B2 | 9/2013 | Aboul-Hosn et al. |
| 8,597,674 B2 | 12/2013 | Chu et al. |
| 8,608,796 B2 | 12/2013 | Matheny |
| 8,637,067 B1 | 1/2014 | Sun et al. |
| 8,673,295 B2 | 3/2014 | Fujimoto et al. |
| 8,679,176 B2 | 3/2014 | Matheny |
| 8,696,744 B2 | 4/2014 | Matheny et al. |
| 8,709,076 B1 | 4/2014 | Matheny et al. |
| 8,771,294 B2 | 7/2014 | Sepetka et al. |
| 8,834,344 B2 | 9/2014 | Aboul-Hosn et al. |
| 8,871,511 B1 | 10/2014 | Matheny et al. |
| 8,877,224 B2 | 11/2014 | Matheny et al. |
| 8,889,791 B2 | 11/2014 | Guan et al. |
| 8,940,292 B2 | 1/2015 | Atala et al. |
| 8,974,542 B2 | 3/2015 | Fujimoto et al. |
| 8,980,296 B2 | 3/2015 | Matheny et al. |
| 9,011,526 B2 | 4/2015 | Matheny |
| 9,023,972 B2 | 5/2015 | Chu et al. |
| 9,044,319 B2 | 6/2015 | Matheny |
| 9,060,969 B2 | 6/2015 | Matheny |
| 9,078,873 B2 | 7/2015 | Matheny |
| 9,078,882 B2 | 7/2015 | Matheny |
| 9,084,841 B2 | 7/2015 | Matheny |
| 9,089,549 B2 | 7/2015 | Matheny |
| 9,119,841 B2 | 9/2015 | Matheny |
| 9,119,899 B2 | 9/2015 | Matheny |
| 9,161,952 B2 | 10/2015 | Matheny et al. |
| 9,510,933 B2 | 12/2016 | Ingham et al. |
| 2008/0260831 A1 | 10/2008 | Badylak et al. |
| 2011/0165676 A1 | 7/2011 | Hopkins |
| 2011/0184439 A1 | 7/2011 | Anderson et al. |
| 2013/0202563 A1 | 8/2013 | Badylak et al. |

FOREIGN PATENT DOCUMENTS

| | | |
|---|---|---|
| CN | 103705542 A | 4/2014 |
| CN | 104225667 A | 12/2014 |
| CN | 104837494 A | 8/2015 |
| CN | 104971380 A | 10/2015 |
| WO | 2015143310 A1 | 9/2015 |

OTHER PUBLICATIONS

Badylak et al., "Small intestinal submucosa: a substrate for in vitro cell growth", J Biomater. Sci. Polym. Edn., 1998, vol. 9(8), pp. 863-878.

Badylak, "The extracellular matrix as a biologic scaffold material", Biomaterials, 2007, vol. 28, pp. 3587-3593.

Badylak et al., "Extracellular matrix as a biological scaffold material: Structure and function", Acta Biomaterialia, 2009, vol. 5, pp. 1-13.

Boccafoschi et al., "Decellularized biological matrices: an interesting approach for cardiovascular tissue repair and regeneration", J Tissue Eng Regen Med, 2015, pp. 1648-1657.

Freytes et al., "Preparation and rheological characterization of a gel form of the porcine urinary bladder matrix," Biomaterials, 2008, vol. 29, pp. 1630-1637.

Gilbert et al., "Decellularization of tissues and organs", Biomaterials, 2006, vol. 27, pp. 3675-3683.

Green, "Abstracts From the 14th Biennial Meeting of the International Society for Applied Cardiovascular Biology," Cardiovascular Pathology, 2014, vol. 23, pp. e1-e-29.

Hiles et al., "Porosity of porcine small-intestinal submucosa for use as a vascular graft", Journal of Biomedical Materials Research, 1993, vol. 27, pp. 139-144.

Hodde et al., "Vascular Endothelial Growth Factor in Porcine-Derived Extracellular Matrix", Endothelium, 2001, vol. 8(1), pp. 11-24.

Jadlowiec et al., "Pregnancy-Associated Plasma Protein-A is Involved in Matrix Mineralization of Human Adult Mesenchymal Stem Cells and Angiogenesis in the Chick Chorioallontoic Membrane", Endocrinology, 2005, vol. 146(9), pp. 3765-3772.

Andenhed et al., "Risk Profiles for Aortic Dissection and Ruptured or Surgically Treated Aneurysms: A Prospective Cohort Study", J Am Heart Assoc., 2015, vol. 4, pp. e001513.

Medberry et al., "Hydrogels derived from central nervous system extracellular matrix", Biomaterials, 2013, vol. 34, pp. 1033-1040.

Morin et al., "In Vitro Models of Angiogenesis and Vasculogenesis in Fibrin Gel", Exp Cell Res, 2013, vol. 319(16), pp. 2409-2417.

Passaniti et al., "A Simple, Quantitative Method for Assessing Angiogenesis and Antiangiogenic Agents Using Reconstituted Basement Membrane, Heparin, and Fibroblast Growth Factor", Laboratory Investigation, 1992, vol. 67(4), pp. 519-528.

Phillippi et al., "Mechanism of Aortic Medial Matrix Remodeling is Distinct in Bicuspid Aortic Valve Patients", J Thorac Cardiovasc Surg., 2014, vol. 147(3), pp. 1056-1064.

Rajangam et al., "Fibrinogen and fibrin based micro and nano scaffolds incorporated with drugs, proteins, cells and genes for therapeutic biomedical applications", International Journal of Nanomedicine, 2013, vol. 8, pp. 3641-3662.

Reing et al., "Degradation Products of Extracellular Matrix Affect Cell Migration and Proliferation", Tissue Engineering: Part A, 2009, vol. 15(3), pp. 605-614.

Sawkins et al., "Hydrogels derived from demineralized and decellularized bone extracellular matrix", Acta Biomaterialia, 2013, vol. 9, pp. 7865-7873.

Smith et al., "Improved Growth Factor Directed Vascularization into Fibrin Constructs Through Inclusion of Additional Extracellular Molecules", Microvasc Res., 2007, vol. 73(2), pp. 84-94.

Smith et al., "The use of quantum dots for analysis of chick CAM vasculature", Microvascular Research, 2007, vol. 73, pp. 75-83.

Wang et al., "Preparation and characterization of pro-angiogenic gel derived from small intestinal submucosa", Acta Biomaterialia, 2016, vol. 29, pp. 135-148.

Wolf et al., "A Hydrogel Derived From Decellularized Dermal Extracellular Matrix", Biomaterials, 2012, vol. 33(29), pp. 7028-7038.

Zimmerlin et al., "Stromal vascular progenitors in adult human adipose tissue", Cytometry, 2010, vol. 77(1), pp. 22-30.

Yang et al., "Role of Adventitial Fibroblasts and Their Reduced Nicotinamide Adenine Dinucleotide Phosphate Oxidase Activation in Vascular Injury", Chinese Circulation Journal, 2015, vol. 30, No. 4, pp. 404-407. English Language abstract.

Dall'olmo et al., "Blood Vessel-Derived Acellular Matrix for Vascular Graft Application", Biomed Res Int. 2014; vol. 2014, Article ID: 685426.

Conklin et al., "Development and evaluation of a novel decellularized vascular xenograft", Medical Engineering & Physics, 2002, vol. 24(3), pp. 173-183.

(56) References Cited

OTHER PUBLICATIONS

Stegemann et al., "Review: Advances in Vascular Tissue Engineering Using Protein-Based Biomaterials", Tissue Eng., 2007, vol. 13(11), pp. 2601-2613.

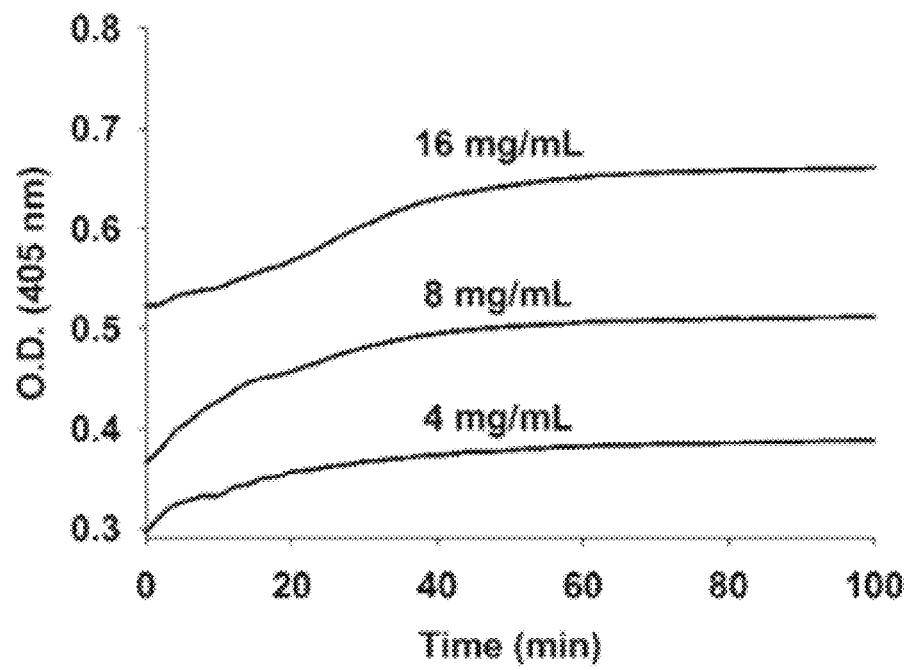
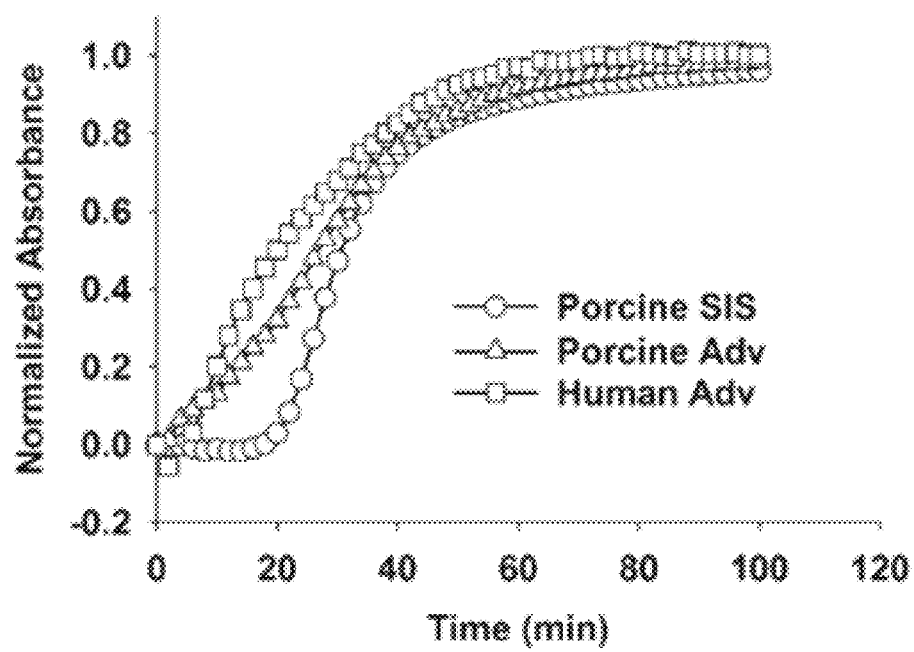
Fig. 11

|  |  |  | Porcine | | Human | |
| --- | --- | --- | --- | --- | --- | --- |
| Array Key | Protein | Gene ID | Adventitia Mean (S.D.) | SIS Mean (S.D.) | Adventitia-Normal Aorta Mean (S.D.) | Adventitia-Aneurysmal Aorta Mean (S.D.) |
| A1, A2 | Reference spots | N/A | - | - | - | - |
| A5, A6 | Activin A | 3624 | 44.9 (0.27) | 44.5 (0.08) | 25.6 (0.52) | 22.2 (0.14) |
| A7, A8 | ADAMTS-1 | 9510 | 43.7 (0.56) | 47.2 (2.41) | 20.6 (0.09) | 18.4 (0.33)# |
| A9, A10 | Angiogenin | 283 | 42.5 (0.09) | 51.4 (1.27) | 23.3 (0.07) | 18.5 (0.30)# |
| A11, A12 | Angiopoietin-1 | 284 | 43.6 (0.41) | 47.3 (1.51) | 21.2 (0.06) | 18.7 (0.30) |
| A13, A14 | Angiopoietin-2 | 258 | 45.5 (0.17) | 47.8 (0.03)* | 23.2 (0.05) | 20.1 (0.24)# |
| A15, A16 | Angiostatin/Plasminogen | 5340 | 42.9 (0.22) | 43.5 (0.61) | 19.8 (0.00) | 17.7 (0.32) |
| A17, A18 | Amphiregulin | 374 | 43.8 (0.32) | 43.7 (0.20) | 20.7 (0.09) | 18.0 (0.15)# |
| A19, A20 | Artemin | 9048 | 44.7 (0.08) | 43.6 (0.34) | 22.6 (0.35) | 19.9 (0.05)# |
| A23, A24 | Reference spots | N/A | - | - | - | - |
| B1, B2 | Coagulation factor III | 2152 | 44.3 (0.44) | 44.0 (0.71) | 20.2 (0.60) | 18.7 (0.09) |
| B3, B4 | CXCL16 | 58191 | 42.5 (0.24) | 43.6 (0.36) | 21.2 (0.49) | 21.4 (0.30) |
| B5, B6 | DPPIV | 1803 | 44.0 (0.05) | 41.3 (0.51) | 17.2 (0.05) | 16.7 (0.13) |
| B7, B8 | EGF | 1950 | 44.7 (0.08) | 44.9 (1.88) | 19.2 (0.23) | 18.3 (0.22)# |
| B9, B10 | EG-VEGF | 84432 | 46.3 (0.03) | 50.8 (1.58) | 20.2 (0.15) | 19.5 (0.20) |
| B11, B12 | Endoglin | 2022 | 44.0 (0.27) | 45.4 (1.47) | 20.6 (0.17) | 18.6 (0.20)# |
| B13, B14 | Endostatin/Col 18 | 80781 | 42.2 (0.11) | 43.9 (0.09)* | 20.0 (0.31) | 19.7 (0.04) |
| B15, B16 | Endothelin-1 | 1906 | 44.9 (0.40) | 45.6 (0.67) | 22.2 (0.48) | 21.5 (0.22) |
| B17, B18 | FGF-acidic | 2246 | 43.3 (0.70) | 122.0 (4.43)* | 21.7 (0.05) | 19.5 (0.18)# |
| B19, B20 | FGF-basic | 2263 | 43.5 (0.46) | 100.2 (0.56)* | 22.9 (0.00) | 20.6 (0.01)# |
| B21, B22 | FGF4 | 2249 | 44.6 (0.18) | 43.4 (0.74) | 20.3 (0.26) | 18.2 (0.37)# |
| B23, B24 | FGF7 | 2252 | 43.9 (0.38) | 45.0 (0.70) | 19.8 (0.22) | 19.7 (0.00) |
| C1, C2 | GDNF | 2668 | 43.7 (0.74) | 44.7 (0.79) | 20.0 (0.13) | 18.0 (0.58) |
| C3, C4 | GM-CSF | 1437 | 44.4 (0.16) | 43.9 (0.31) | 22.9 (0.34) | 22.2 (0.49) |
| C5, C6 | HB-EGF | 1839 | 45.1 (0.16) | 43.7 (0.06)* | 20.4 (0.19) | 19.7 (0.19) |
| C7, C8 | HGF | 3082 | 44.6 (0.84) | 46.0 (1.17) | 22.1 (0.03) | 20.6 (0.51) |
| C9, C10 | IGFBP-1 | 3484 | 44.9 (0.10) | 50.1 (0.53)* | 22.0 (0.04) | 21.1 (0.06)# |
| C11, C12 | IGFBP-2 | 3485 | 42.2 (0.25) | 44.6 (1.19) | 19.5 (0.10) | 18.3 (0.05)# |
| C13, C14 | IGFBP-3 | 3486 | 45.5 (0.37) | 45.7 (0.16) | 22.1 (0.22) | 21.3 (0.13) |
| C15, C16 | IL1-β | 3553 | 42.8 (0.22) | 43.1 (0.16) | 19.2 (0.21) | 18.7 (0.23) |
| C17, C18 | IL-8 | 3576 | 42.0 (0.05) | 45.7 (0.50) | 19.4 (0.02) | 18.5 (0.17) |
| C19, C20 | LAP (TGF-β1) | 7040 | 41.5 (1.52) | 46.0 (0.61) | 22.1 (0.08) | 20.0 (0.19)# |
| C21, C22 | Leptin | 3952 | 43.3 (0.09) | 43.6 (0.91) | 21.8 (0.12) | 19.8 (0.04)# |
| C23, C24 | MCP-1 | 6347 | 43.1 (0.79) | 44.6 (0.28) | 23.2 (0.22) | 20.8 (0.61) |
| D1, D2 | MIP-1α | 6348 | 43.8 (0.13) | 44.8 (0.52) | 22.4 (0.12) | 20.9 (0.01)# |
| D3, D4 | MMP-8 | 4317 | 43.6 (0.31) | 43.3 (0.15) | 21.1 (0.85) | 20.8 (0.47) |
| D5, D6 | MMP-9 | 4218 | 44.9 (0.04) | 44.4 (0.39) | 21.1 (0.09) | 21.0 (0.02) |
| D7, D8 | NRG1-β1 | 3084 | 43.2 (0.28 ) | 44.3 (1.45) | 20.9 (0.02) | 20.3 (0.33) |

*Fig. 16A*

| Array Key | Protein | Gene ID | Porcine Adventitia Mean (S.D.) | Porcine SIS Mean (S.D.) | Human Adventitia Mean (S.D.) | Human SIS Mean (S.D.) |
|---|---|---|---|---|---|---|
| D9, D10 | Pentraxin 3 | 5806 | 44.5 (0.36) | 48.8 (0.07)* | 21.7 (0.16) | 21.3 (0.18) |
| D11, D12 | PD-ECGF | 1890 | 46.3 (0.23) | 46.8 (1.67) | 21.7 (0.51) | 21.3 (0.38) |
| D13, D14 | PDGF-AA | 5154 | 44.7 (0.12) | 44.4 (0.05) | 21.6 (0.04) | 21.0 (0.15) |
| D15, D16 | PDGF-BB | 5155 | 41.6 (0.19) | 42.3 (0.32) | 18.5 (0.41) | 18.5 (0.26) |
| D17, D18 | Persephin | 5623 | 45.0 (0.11) | 44.7 (0.63) | 22.9 (0.24) | 21.4 (0.10)# |
| D19, D20 | Platelet factor 4 | 5196 | 41.8 (0.66) | 43.2 (0.07) | 21.9 (0.13) | 19.5 (0.43) |
| D21, D22 | PlGF | 5228 | 47.0 (0.47) | 48.5 (0.25) | 25.5 (0.32) | 22.9 (0.14)# |
| D23, D24 | Prolactin | 5617 | 42.6 (0.34) | 44.2 (0.81)* | 21.6 (0.50) | 19.5 (0.16) |
| E1, E2 | Serpin B5 | 5268 | 41.8 (0.51) | 48.4 (0.44)* | 23.2 (0.25) | 21.5 (0.17)# |
| E3, E4 | Serpin E1 | 5054 | 42.4 (0.69) | 43.2 (0.47) | 22.5 (0.46) | 20.6 (0.49) |
| E5, E6 | Serpin F1 | 5176 | 43.2 (0.21) | 44.0 (0.18) | 21.6 (0.15) | 22.2 (1.00) |
| E7, E8 | TIMP-1 | 7076 | 43.7 (0.19) | 44.6 (1.09) | 20.3 (0.25) | 19.5 (0.18) |
| E9, E10 | TIMP-4 | 7079 | 43.8 (0.68) | 47.5 (0.42)* | 21.0 (0.32) | 19.9 (0.52) |
| E11, E12 | Thrombospondin-1 | 7057 | 86.2 (0.22) | 88.9 (3.50) | 63.3 (1.42) | 60.0 (1.91) |
| E13, E14 | Thrombospondin-2 | 7058 | 43.5 (1.09) | 44.0 (0.08) | 21.1 (0.05) | 20.8 (0.07) |
| E15, E16 | uPA | 5328 | 43.1 (0.77) | 45.2 (0.15) | 20.5 (0.45) | 20.5 (0.32) |
| E17, E18 | Vasohibin | 22846 | 44.7 (0.27) | 44.1 (0.30) | 21.2 (0.39) | 20.3 (0.16) |
| E19, E20 | VEGF | 7422 | 44.1 (0.44) | 44.2 (0.38) | 22.0 (0.29) | 19.9 (0.33)# |
| E21, E22 | VEGF-C | 7424 | 45.5 (0.03) | 44.4 (0.49) | 21.0 (0.00) | 18.7 (0.31) |
| F1, F2 | Reference spots | N/A | - | - | - | - |
| F23, F24 | Negative control spots | N/A | - | - | - | - |

*Fig. 16B*

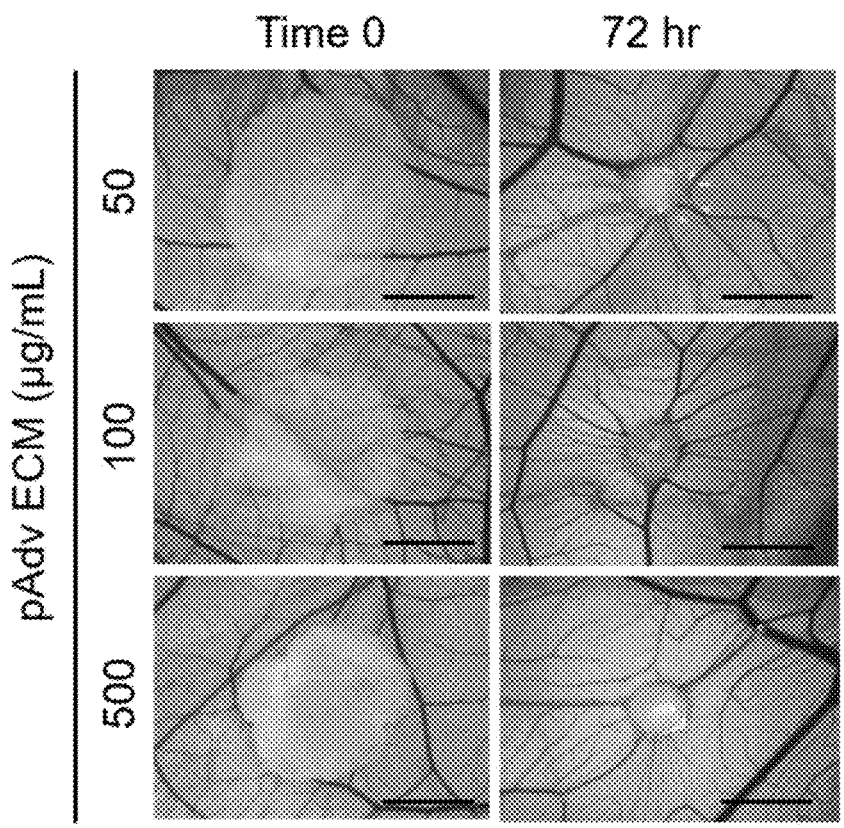

*Fig. 17*

VASCULAR EXTRACELLULAR MATRIX HYDROGEL

CROSS REFERENCE TO RELATED APPLICATIONS

This is a divisional of U.S. patent application Ser. No. 16/070,044, filed Jul. 13, 2018, which is the United States national phase of International Application No. PCT/US2017/013355, filed Jan. 13, 2017, and claims the benefit of U.S. Provisional Patent Application No. 62/278,065, filed Jan. 13, 2016, the contents of which are incorporated herein by reference in their entirety.

Provided herein is a method of making a vascular ECM material, such as a gel, a vascular ECM material, and method of use of the vascular ECM material, for example for treatment of aneurysms and for vascularization or re-vascularization.

Free rupture or dissection of the ascending aorta is a concerning clinical problem that occurs in up to 2.5 million patients per year worldwide. Such aortic catastrophe is often fatal, can occur without warning, and the only treatment option is emergent aortic replacement. This biomechanical weakening of the aortic wall is often precipitated by formation of thoracic aortic aneurysm (TAA). TAA involves medial matrix degeneration but the inciting mechanisms of aneurysm formation are mostly unknown. Furthermore, there are currently no known strategies to regenerate tissue deficits in the aortic wall. Remodeling of the vasa vasorum, the microvascular network in the adventitia and decreased expression of angiogenic signaling targets are associated with TAA.

Extracellular matrix (ECM) bioscaffolds are tissue-specific biomaterials with inherent bioactivity and native structural features. These properties enable their desirable use as three-dimensional in vitro cell culture substrates for biologic discovery of cellular mechanisms or as disease models. Certain decellularized tissues show promise for therapeutic tissue regeneration in a variety of applications. Development of decellularized native tissues has led to the production of tissue-engineered scaffolds which retained basement membrane proteins such as collagen type IV, laminin, and fibronectin that enhance cellular adhesion and invoke signaling to influence cellular differentiation and regenerative potential. Growth factors including transforming growth factor-beta, basic fibroblast growth factor (FGF), hepatocyte growth factor and vascular endothelial growth factor (VEGF) persist in their bioactive form within ECM bioscaffolds after sterilization. Additionally, degradation of ECM bioscaffolds releases matricryptic peptides that invoke biologic activity. ECM bioscaffolds guide stem cell differentiation through growth factor retention and unique matrix compliance, which together comprise tissue-specific microenvironments that are advantageous for regeneration.

STATEMENT REGARDING FEDERAL FUNDING

This invention was made with government support under Grant Nos. HL127214 and HL109132 awarded by the National Institutes of Health. The government has certain rights in the invention.

SUMMARY

Provided therefore are methods for preparing hydrogels from solubilized vasculature-derived extracellular matrix (ECM) compositions useful as in vitro cell culture substrates or in vivo biomaterials for tissue repair in cardiovascular applications. The extracellular matrix (ECM) of blood vessels provides essential signaling for tissue-specific cell behavior including maintenance of cell phenotype, differentiation, stem cell self-renewal, and regulates overall tissue homeostasis and function. This invention embodies a method wherein decellularized ECMs from blood vessels (e.g. porcine or human aorta adventitia in one aspect) are formulated into hydrogels and can be used as substrates for in vitro cell culture and in vivo tissue regeneration.

The compositions and methods described herein solve the problem of inadequate biomaterials to promote vasculogenesis. In one aspect, provided herein is a native biologic substrate for discovery biology in the aortic wall and its associated microvasculature. The benefit of the compositions and methods provided herein is that it is more representative of native physiology than current products in the research marketplace (e.g. Matrigel). The described compositions and methods are useful for providing a research product for discovery biology and for the potential for clinical translation as a therapeutic biological material for the treatment of cardiovascular pathologies.

The compositions and methods provided herein utilize vascular extracellular matrix (ECM) as the starting material for the hydrogel and in one aspect, contain no synthetic polymer components or cells. A unique advantage is the availability from porcine, ovine or bovine sources. As indicated below, vascular ECM, e.g. aortic adventitial tissue, requires a unique method of derivation and formulation to produce a hydrogel.

BRIEF DESCRIPTION OF THE DRAWINGS

FIG. 11. Turbidimetric gelation kinetics of ECM hydrogels. Gelation of pH-neutralized ECM digests was monitored using optical density (O.D.) readings at 405 nm at 37° C. for 90 min. A) Porcine adventitia (Adv) (4, 8 and 16 mg/mL). B) Normalized turbidimetric gelation kinetics of porcine SIS (8 mg/mL), human Adv and porcine Adv (16 mg/mL).

FIG. 13A—Human adventitia-derived endothelial cells were cultured on growth factor reduced-Matrigel substrates: (A) DMSO, 0.05% (v/v), (B) Digestion buffer (1% (w/v) Pepsin in 0.1 N HCl), (C) pAdv ECM, and (D) pSIS ECM. FGF2 inhibitor PD173074 (100 nM) was added to the culture medium of above treatments shown in parallel wells (E-H). A-H: One representative 10× field is shown, selected from one of three replicates of two independent experiments. All scale bars=50 µm for (A-H). Quantification of the number (FIG. 13B) and total length (FIG. 13C) of tube-like structures from 5×5 stitched fields captured at 10× for non-ECM-supplemented (open bars), pAdv (solid bars) and pSIS (gray bars) ECM-supplemented substrates in the absence and presence of PD173074. Bars represent mean of three assay replicates ±standard deviation. Images and graphs represent data from one of two independent experiments. *Significant from pepsin HCl, p<0.02; #Significant from pAdv ECM-treated cells in the absence of PD173074, p<0.03.

FIG. 14A) Representative bright field images of scaffolds before (Time 0) and after (72 hr) incubation on the chorioallantoic membrane (CAM) of the chick embryo. The pro-angiogenic response to pSIS and pAdv ECM-containing fibrin scaffolds (250µg/mL) is revealed by the spoke-wheel pattern along the perimeter of the scaffolds. There was no appreciable angiogenic response detected around scaffolds loaded with digestion buffer (1% (w/v) pepsin in 0.1 N HCl) or DMSO. Addition of the FGF2 inhibitor PD173074 (100 nM) abrogated the angiogenic response to pAdv ECM. Addition of the inhibitor vehicle only (DMSO) did not alter the angiogenic response to pAdvECM. All scale bars for FIG. 14A=5 mm. FIG. 14B) Representative histological cross-sections of CAM assay scaffolds. The CAM vasculature was visualized using injected tomato lectin-Dylight® 650 (red) and nuclei are labeled with Hoechst dye (blue). A dashed white line denotes the scaffold/CAM interface. Scaffolds loaded with digestion buffer alone exhibited no vessel invasion. pSIS ECM (250 µg/mL) stimulated invasion of new vasculature (denoted by arrowheads) toward the scaffold as did pAdv ECM in a dose-dependent manner for concentrations 50-250 µg/mL. The maximum tested dose of pAdv ECM (500 µg/mL) inhibited invasion of blood vessels into the scaffold. FIG. 14C) Addition of DMSO did not alter pAdvECM induced invasion of blood vessels and FGF2 inhibitor PD173074 blocked the effect of pAdv ECM loaded scaffolds. All scale bars in FIG. 14B and FIG. 14C=500 *Avascular zone comprised of lectin-negative cells. FIG. 14D). Representative histological cross-sections showing chemoattraction of lectin-negative cells in an avascular zone (*) adjacent to invading lectin-positive cells (arrowheads) in pAdvECM loaded fibrin scaffold (250 µg/mL) (i) and inhibition of invasion of lectin-positive cells in 500 µg/ml pAdv ECM-loaded fibrin scaffold (ii). (*) avascular zone comprised of lectin-negative cells. All scale bars for FIG. 14D=20 µm.

FIGS. 16A and 16B: Angiogenesis-related protein array. Decellularized adventitia from normal (n=7 patients pooled) and aneurysmal (n=28 pooled patients) human aorta, porcine adventitia and SIS were analyzed for 55 angiogenesis-related proteins. Values represent mean pixel density of two assay replicates ±standard deviation (S.D.) for chemiluminescence detected after 5 (human ECMs) or 14 (porcine ECMs) minutes of exposure. * p<0.05 when compared with porcine adventitia; #p<0.05 when compared with normal human aortic adventitial specimens.

FIG. 17. Representative bright-field images of scaffolds before (Time 0) and after (72 hr) incubation on CAM. Angiogenic response shown by the spoke-wheel appearance of vessels around fibrin scaffolds loaded with all doses of pAdv ECM (50, 100 and 500 μg/mL). (All scale bars=5 mm.

DETAILED DESCRIPTION

Figure 1:
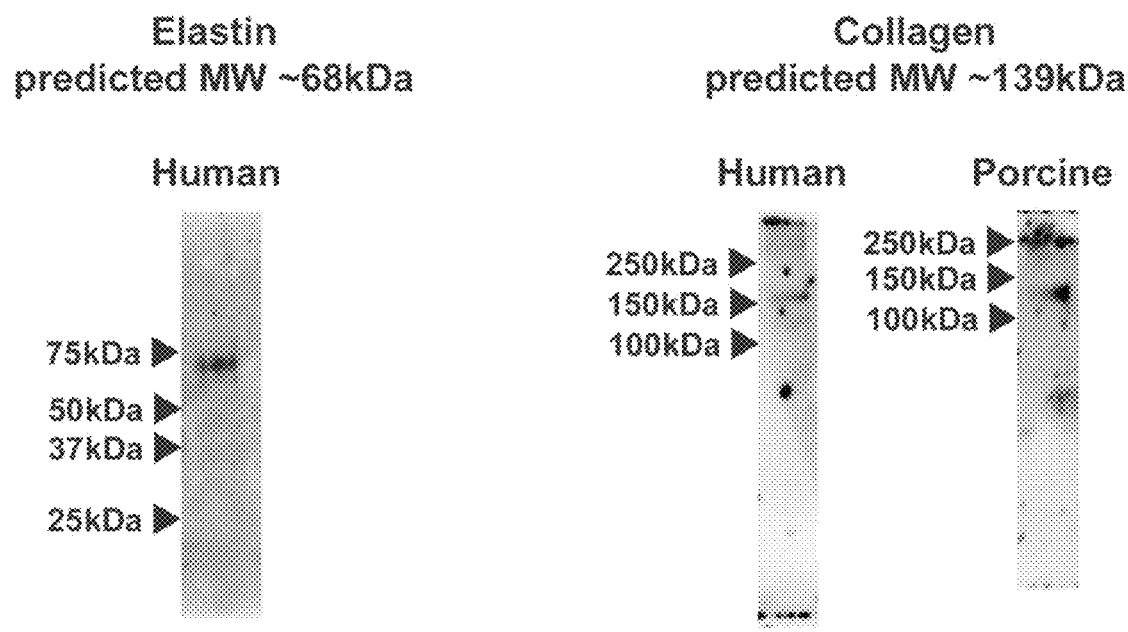
FIG. 1 provides photographs of western blotting analysis for elastin and type I collagen of the adventitial ECM (AdvECM) gel preparation of Example 1.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases. As used herein "a" and "an" refer to one or more.

As used herein, the term "patient" or "subject" refers to members of the animal kingdom including but not limited to human beings and "mammal" refers to all mammals, including, but not limited to human beings.

As used herein, the "treatment" or "treating" of a wound or defect means administration to a patient by any suitable dosage regimen, procedure and/or administration route of a composition, device or structure with the object of achieving a desirable clinical/medical end-point, including attracting progenitor cells, healing a wound, correcting a defect, etc.

As used herein, the terms "comprising," "comprise" or "comprised," and variations thereof, are open-ended and do not exclude the presence of other elements not identified. In contrast, the term "consisting of" and variations thereof is intended to be closed-ended, and excludes additional elements in anything but trace amounts.

As used herein, the terms "extracellular matrix" and "ECM" refer to a natural scaffolding for cell growth. ECM is a complex mixture of structural and non-structural biomolecules, including, but not limited to, collagens, elastins, laminins, glycosaminoglycans, proteoglycans, antimicrobials, chemoattractants, cytokines, and growth factors. In mammals, ECM often comprises about 90% collagen, in its various forms. The composition and structure of ECMs vary depending on the source of the tissue. For example, small intestine submucosa (SIS), urinary bladder matrix (UBM), liver stroma ECM, and dermal ECM each differ in their overall structure and composition due to the unique cellular niche needed for each tissue.

The ECM materials as described herein retain activity of at least a portion of its structural and non-structural biomolecules, including, but not limited to, collagens, elastins, laminins, glycosaminoglycans, proteoglycans, antimicrobials, chemoattractants, cytokines, and/or growth factors, such as, without limitation, the adventitial ECM product as described in the examples below. The activity of the biomolecules within the ECM can be removed chemically or mechanically, for example, by cross-linking and/or by dialyzing the ECM. In one aspect, the ECM materials described herein essentially have not been cross-linked and/or dialyzed, meaning that the ECM has not been subjected to a dialysis and/or a cross-linking process, or conditions other than decellularization processes or processes that occur as part of storage and handling of ECM prior to solubilization, as described herein. Thus, in one aspect, the ECM material is not cross-linked and/or dialyzed in anything but a trivial manner which does not substantially affect the gelation and functional characteristics of the ECM material in its uses described herein.

ECM is prepared by the decellularization and/or devitalization of tissues prior to use. In one aspect, decellularization is performed to prevent a pro-inflammatory response. As such, in one aspect, a decellularized or devitalized ECM product refers to ECM material that is decellularized to the extent that a pro-inflammatory response, and thus growth of fibrotic tissue is not elicited to any substantial degree in favor of constructive remodeling.

By "bio compatible", it is meant that a device, scaffold composition, etc. is essentially, practically (for its intended use) and/or substantially non-toxic, non-injurious or non-inhibiting or non-inhibitory to cells, tissues, organs, and/or organ systems that would come into contact with the device, scaffold, composition, etc.

As used herein, the term "derive" and any other word forms or cognates thereof, such as, without limitation, "derived" and "derives", refers to a component or components obtained from any stated source by any useful method. For example and without limitation, generically, an ECM-derived gel refers to a gel comprised of components of ECM obtained from any tissue by any number of methods known in the art for isolating ECM. In another example, mammalian tissue-derived ECM refers to ECM comprised of components of a particular mammalian tissue obtained from a mammal by any useful method.

The methods described herein involve preparation of ECM or an ECM gel. The ECM gel is reverse gelling, or can be said to exhibit reverse thermal gelation, in that it forms a gel upon an increase in temperature. As the temperature rises above a certain temperature in a reverse gel, a hydrogel is formed. The general concept of reverse gelation of polymers and, e.g., its relation to lower critical solution temperature (LCST) are broadly known in the chemical arts. The ECM compositions described herein are prepared, for example, from decellularized or devitalized, intact ECM as described below. An ECM gel is prepared by digestion of the ECM material with an acid protease, neutralization of the material to form a pre-gel, and then raising the temperature of the pre-gel above a gelation temperature, for example the LCST of the pre-gel, to cause the pre-gel to gel. As used herein, the term "gel" includes hydrogels. The transition temperature for acid-protease-digested from solution to gel is typically within the range of from 10° C. to 40° C. and any increments or ranges therebetween, for example from 20° C. to 35° C. For example, the pre-gel can be warmed to 37° C. to form a hydrogel.

Tissue for preparation of ECM, ECM-derived pre-gel solutions, and gels as described herein may be harvested in any useful manner. According to various aspects, the ECM materials described herein are prepared from vascular adventitia, such as arterial or aortic adventitia. For example and without limitation, in one aspect, the ECM material is prepared from harvested porcine aorta, and in another, from human aorta. The adventitia is dissected from the harvested tissue and is optionally frozen. Aorta tissue is obtained by any suitable method, for example by manually isolating from the surrounding tissue. In one aspect, the aortic tissue is not obtained from aneurysmal tissue.

Decellularized or devitalized ECM can be dried, either lyophilized (freeze-dried) or air dried. The ECM composition is optionally comminuted at some point, for example prior to acid protease digestion in preparation of an ECM gel, for example prior to or after drying. The comminuted ECM can also be further processed into a powdered form by methods, for example and without limitation, such as grinding or milling in a frozen or freeze-dried state. As used herein, the term "comminute" and any other word forms or cognates thereof, such as, without limitation, "comminution" and "comminuting", refers to the process of reducing larger particles, e.g., of dried ECM, into smaller particles, including, without limitation, by tearing, grinding, blending, shredding, slicing, milling, cutting, shredding, shearing, and pulverizing. ECM can be comminuted while in any form, including, but not limited to, hydrated forms, frozen, air-dried, lyophilized, powdered, sheet-form.

In order to prepare solubilized ECM tissue, ECM, for example comminuted ECM, is digested with an acid protease in an acidic solution to form a digest solution. As used herein, the term "acid protease" refers to an enzyme that cleaves peptide bonds, wherein the enzyme has increased activity of cleaving peptide bonds in an acidic pH. For example and without limitation, acid proteases include pepsin and trypsin and mixtures thereof.

As an example, the digest solution of ECM is kept at a constant stir for a certain amount of time at room temperature. In one aspect, the pH is maintained at less than pH 4.0 or at pH 2.0±0.3 during acid protease digestion of the decellularized aortic adventitial tissue as described herein. The ECM digest can be used immediately or can be stored at −20° C. or frozen at, for example and without limitation, −20° C. or −80° C. In certain aspects, the ECM digest is snap frozen in liquid nitrogen. To form a "pre-gel" solution, the pH of the digest solution is raised to a pH between 6.8 and 7.8. The pH can be raised by adding one or more of a base or an isotonic buffered solution, for example and without limitation, NaOH or PBS at pH 7.4. The method optionally does not include a dialysis step prior to gelation, yielding a more-complete ECM-like matrix that typically gels at 37° C. more slowly than comparable collagen or dialyzed ECM preparations. The gel therefore retains more of the qualities of native ECM due to retention of many native soluble factors, such as, without limitation, cytokines. These factors contribute to chemoattraction of cells and proper rearrangement of tissue at the site of injury, rather than a fibrotic response that leads to unwanted scarring. In other embodiments, the ECM is dialyzed prior to gelation to remove certain soluble components.

As used herein, the term "isotonic buffered solution" refers to a solution that is buffered to a pH between 6.8 and 7.8, e.g., pH 7.4, and that has a balanced concentration of salts to promote an isotonic environment. As used herein, the term "base" refers to any compound or a solution of a compound with a pH greater than 7. For example and without limitation, the base is an alkaline hydroxide or an aqueous solution of an alkaline hydroxide. In certain embodiments, the base is NaOH, or NaOH in PBS. This "pre-gel" solution can, at that point be incubated at a suitably warm temperature, for example and without limitation, at about 37° C. to gel.

In the method of preparing an ECM gel, the ECM may be partially or completely digested with the acid protease, such as pepsin. The digested ECM is then neutralized to a pH of 6.8-7.8, e.g., 7.2-7.6, or 7.4 and the neutralized and digested ECM material is gelled by incubation at a temperature at which the material gels, e.g., at a temperature above 20, 25, 30, or 35° C., such as at 37°. The degree of digestion can be determined by comparison on a gel, or by ascertaining the degree of degradation of hyaluronic acid, for example by Western blot (anti-hyaluronic acid antibodies are commercially-available from multiple sources) or chromatographic methods, as are broadly known. For example in a partial digestion, hyaluronic acid is digested less than 50%, 40%, 30%, 25%, 20% or 10%.

Therefore, according to one aspect of the invention, an ECM composition is provided comprising devitalized, acid-protease-digested aortic adventitial tissue, having a pH of from 6.8 to 7.8. In one aspect, the devitalized, acid-protease-digested aortic adventitial tissue is not dialyzed or chemically crosslinked—meaning at no stage during the processing of intact tissue to produce the devitalized, acid-protease-digested aortic adventitial tissue has the material been dialyzed or cross-linked by addition of a chemical cross-linking agent, as is common in the production of certain devitalized ECM materials.

Figure 10:
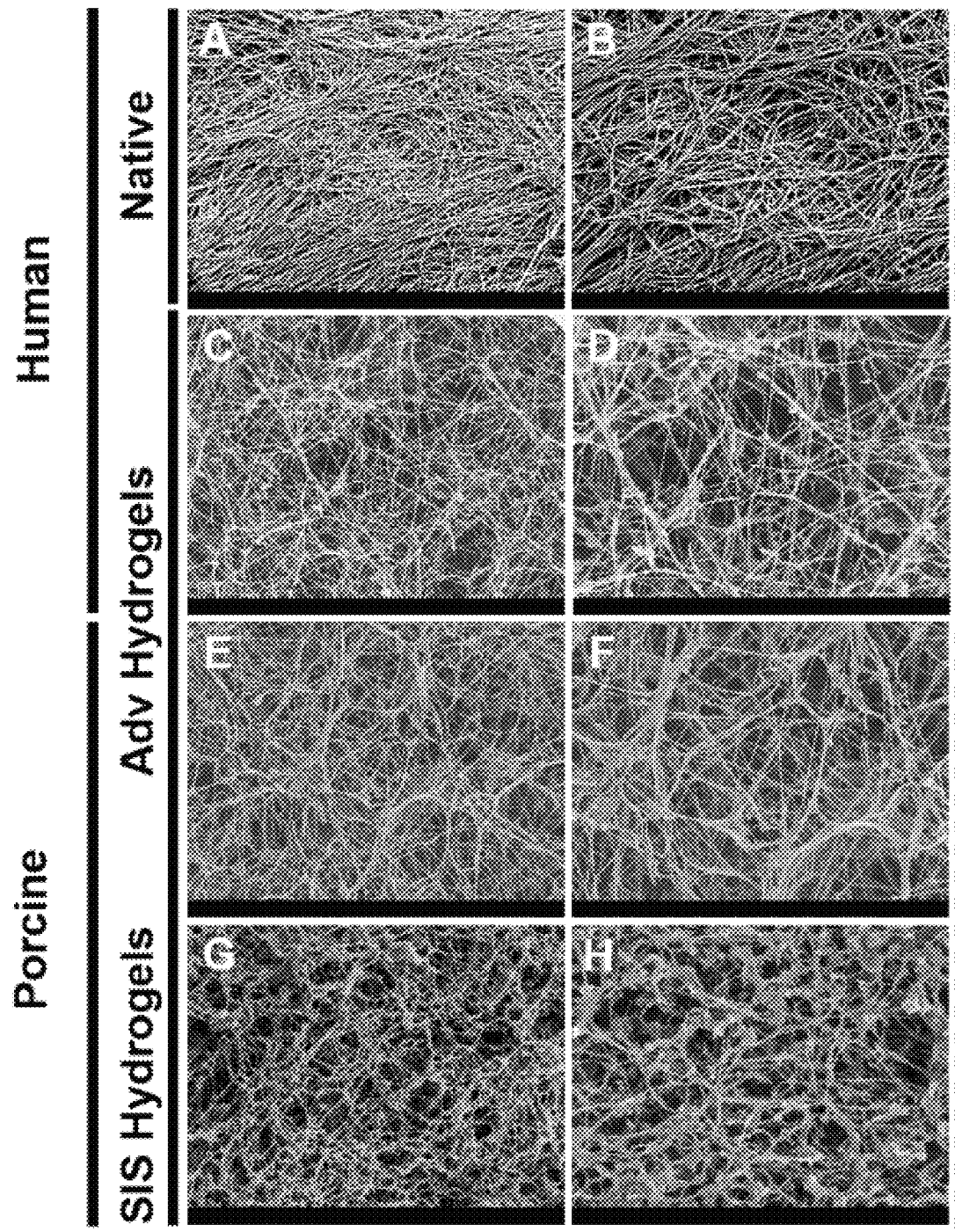
FIG. 10. Scanning electron microscopy of porcine and human adventitial ECM hydrogels. Decellularized tissue and ECM hydrogels were fixed in 2.5% glutaraldehyde and processed for scanning electron microscopy. Representative micrographs showing decellularized human adventitia (Adv) (A-B), human Adv hydrogel (C-D), porcine Adv hydrogel (E-F) and porcine small intestinal submucosa (SIS) hydrogel (G-H) at 5,000× (A, C, E) and 10,000× (B, D, F) magnifications. All scale bars=1 µm.
Figure 15:
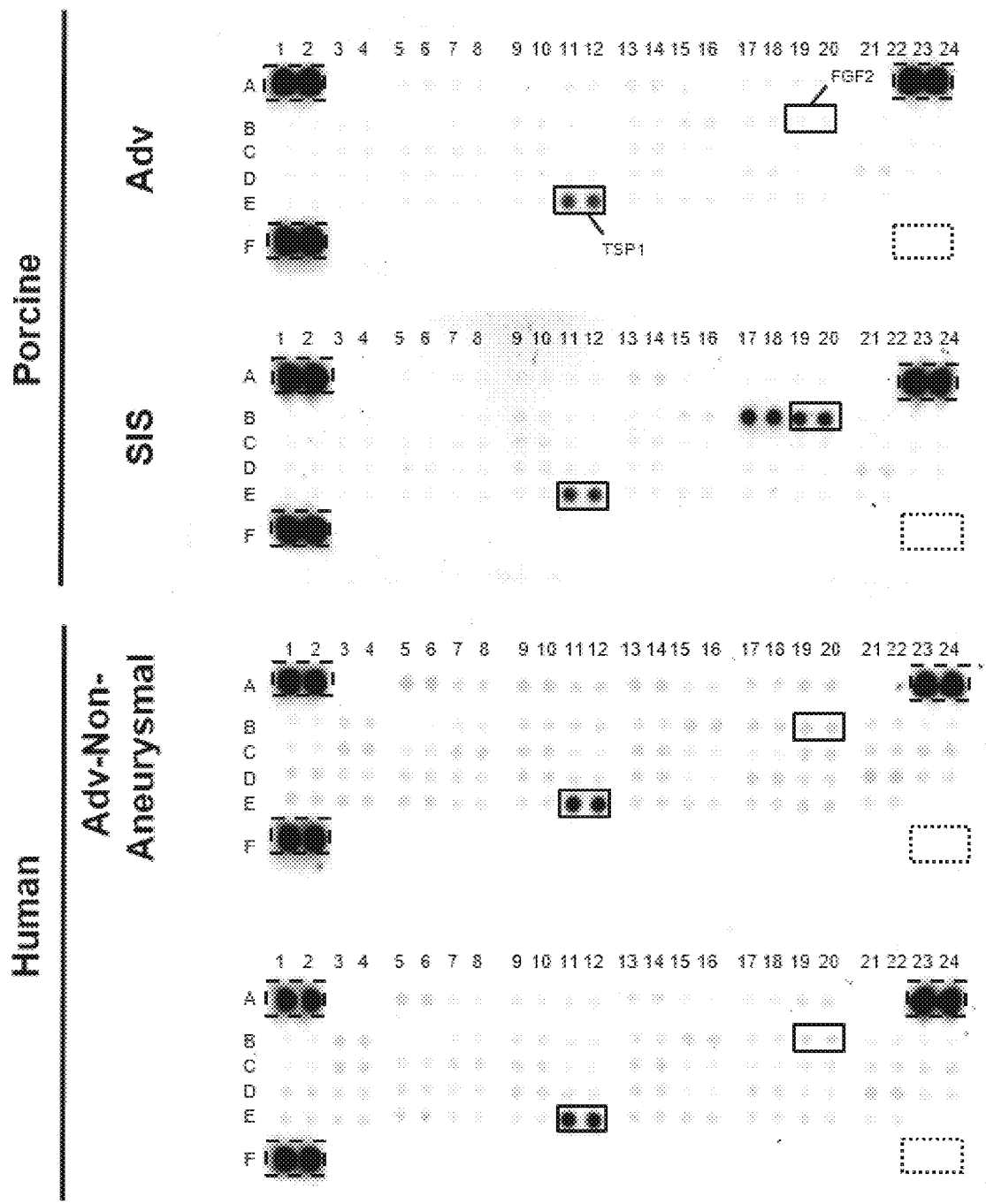
FIG. 15. Protein array-based profile of angiogenesis-related proteins. Lyophilized ECM bioscaffolds (300 µg total protein) were evaluated for the presence of 55 angiogenesis-related proteins in duplicate using the Human Angiogenesis Proteome Profiler Array. Densitometric values are provided in FIG. 16. Images for porcine and human ECM blots reflect exposure times of 20 min and 10 min respectively. Dashed line boxes=positive control reference spots. Dotted line boxes=negative control reference spots.

Unique characteristics of the aortic adventitial ECM composition are described below. In one aspect, the aortic adventitial ECM gel is more porous than comparative ECM gels. For example, in FIG. 10, aortic adventitial ECM gel (panels C-F) is shown to have increased length and linearity of fibers as compared to SIS ECM gel prepared by a comparable method (panels G and H). FIGS. 15 and 16 show the unique composition of the aortic adventitial ECM gel composition as compared to a similarly-prepared SIS ECM gel composition, with significantly lower (at least 50% lower) amounts of FGF-1 and FGF-2, increased amounts of HB-EGF (Heparin Binding EGF Like Growth Factor, 3%), and decreased amounts of various other proteins, e.g. (Ratios of pAdv: pSIS): Angiopoietin 2-0.95; Endostatin—0.96; IGFBP1 (Insulin Like Growth Factor Binding Protein 1)—0.9; PTX3 (Pentraxin 3)—0.91; Prolactin—0.96; Serpin B5—0.87; and TIMP4 (TIMP Metallopeptidase Inhibitor 4)—0.92.

In one aspect, the composition is cell-free, meaning the composition comprises no living cells, and is therefore sterile, and is optionally sterilized or disinfected. The composition can be terminally sterilized, for example by sterilization by, for example and without limitation, exposure to ethylene oxide (EtO) gas, gamma irradiation, or electron beam radiation, and in one aspect when in a dried or lyophilized state (see, e.g., WO 2015/143310, incorporated herein by reference for its technical disclosure of methods of terminally-sterilizing ECM gels). The composition is typically disinfected with peracetic acid, as described herein.

In use, the ECM gel can be injected, sprayed, painted, poured, or otherwise applied to a surface of a tissue, e.g., any blood vessel, that is, the entire vascular network, such as, without limitation: the abdominal aorta or descending aorta; the ascending aorta; the aortic arch; an iliac artery or vein, such as a common, interior, or exterior iliac artery or vein; a carotid artery; a jugular vein; a subclavian artery or vein; a brachiocephalic artery or vein (brachiocephalic trunk artery or vein); the inferior vena cava; superior vena cava; and/or a peripheral blood vessel of a patient. Depending on the final use of the product, the composition may be applied or administered in a variety of ways, either as a dry, e.g., lyophilized powder, a solution, a gel, a foam, etc.

The composition can be administered by itself, or with a device or composition. For example, the composition can be absorbed into, adsorbed onto, mixed into, or otherwise co-administered with a cell-growth scaffold, such as an isotropic or anisotropic mass of fibers of synthetic and/or natural polymer(s), such as an electrodeposited, wet or dry spun, 3D printed, molded, or otherwise formed polymeric structure prepared from biocompatible polymeric materials, as are broadly known in the regenerative medical field, such as collagen, polyester (PE), polyurethane (PU), poly(ester urethane) urea (PEUU), poly(ether ester urethane) urea (PEEUU), poly(ester carbonate urethane)urea PECUU), and poly(carbonate urethane)urea (PCUU) copolymers, and other suitable polymeric materials, such as are disclosed, for example and without limitation in U.S. Pat. Nos. 8,535,719; 8,673,295; 8,889,791; 8,974,542 and 9,023,972.

Additional non-limiting examples of useful polymer compositions for use in the compositions described herein include: polyolefin (polyalkene), polycarbonate, polyanhydride, polyether, polyurea, polyurethane, polyketone, and fluoropolymers. In one aspect, the polymer composition is bioerodible. Non-limiting examples of biocompatible, bioerodible, elastomeric (co)polymer compositions including PEUU, PEEUU, PECUU, and PCUU. Other useful (co) polymers include, without limitation: polymers comprising monomers of alpha-hydroxy acids; polylactides, such as poly(lactide-co-glycolide), poly(L-lactide-co-caprolactone), polyglycolic acid, poly(dl-lactide-co-glycolide), poly(l-lactide-co-dl-lactide); other polyesters including polyhydroxybutyrate, polyhydroxyvalerate, polydioxanone, and polyglactin; polylactones including polycaprolactone; polyglyconate, poly(glycolide-co-trimethylene carbonate), poly(glycolide-co-trimethylene carbonate-co-dioxanone).

The compositions described herein also can be mixed into polymeric compositions prior to or along with deposition of polymeric fibers or formation of structures. Alternatively, where the ECM product is not formed into a gel, ECM gel and/or synthetic polymers may be absorbed into, adsorbed onto or otherwise combined with the ECM product. In one aspect, a composition as described herein is applied to and delivered from an ECM material, such as any commercial ECM material, such as those described herein.

Likewise, the compositions described herein can be applied to or incorporated into, by any suitable method, a non-woven material, such as a bandage, a suture, an implant, such as a ceramic, metal, or polymeric implant, for example a prosthesis, artificial or otherwise-modified vessel, a valve, an intraocular lens, a tissue transplant or implant.

As used herein, the term "coat", and related cognates such as "coated" and "coating," refers to a process comprising of covering an organic, inorganic, or living structure, or combinations thereof, with a composition described herein. For example and without limitation, coating of an inorganic structure with an ECM-derived gel can include methods such as pouring, embedding, layering, dipping, spraying. Ultrasonication may be used to aid in coating of an inorganic structure with the ECM-derived gel. As used herein, the term "ultrasonication" refers to the process of exposing ultrasonic waves typically with a frequency higher than 15 kHz and lower than 400 kHz. Organic structures include both synthetic and natural polymer compositions including devitalized tissue, proteinaceous compositions such as collagen, and synthetic polymer compositions, such as PEUU, PEEUU, PCUU, and PECUU, as indicated above. Living tissue may be any living tissue whether or not located in situ within a patient, or dissected. For example, the compositions and materials described herein may be applied (in situ) to an existing blood vessel, such as the descending aorta, in situ within a patient's abdomen or thoracic cavity. In one aspect, a living, dissected blood vessel is treated with the described compositions, such as soaked, sprayed, and/or wrapped, prior to re-implantation to restore blood flow in a bypass grafting procedure. In one example, the bypass grafting procedure is a cardiac bypass procedure and the composition is applied to, for example and without limitation, a vein, such as a saphenous vein In a further aspect, the composition is combined with other compositions to form a composite structure. The other compositions can be other biocompatible polymer compositions, in which the adventitial ECM gel described herein contains particles of the other biocompatible polymer, or the adventitial ECM gel is dispersed, either homogeneously or non-homogeneously (e.g., as microparticles or nanoparticles) within the other polymer. In one aspect, the other biocompatible polymer is a fibrin plug having gel particles of the described adventitial ECM dispersed throughout. In another aspect, the other biocompatible polymer is a different ECM gel into which the described adventitial ECM gel is mixed either homogeneously or non-homogeneously. Other biocompatible particles include natural polymer compositions, such as, without limitation, fibrin, or synthetic polymers, such as described above.

In another aspect, the composition is coated onto a biocompatible structural material, such as a metal, an inorganic calcium compound such as calcium hydroxide, calcium phosphate or calcium carbonate, or a ceramic composition. Non-limiting examples of suitable metals are cobalt-chrome alloys, stainless steel alloys, titanium alloys, tantalum alloys, titanium-tantalum alloys, which can include both non-metallic and metallic components, such as molybdenum, tantalum, niobium, zirconium, iron, manganese, chromium, cobalt, nickel aluminum and lanthanum, including without limitation, CP Ti (commercially pure titanium) of various grades or Ti 6Al 4V (90% wt. Ti, 6% wt. Al and 4% wt. V), stainless steel 316, Nitinol (Nickel-titanium alloy), titanium alloys coated with hydroxyapatite. Metals are useful due to high strength, flexibility, and biocompatibility. Metals also can be formed into complex shapes and many can withstand corrosion in the biological environments, reduce wear, and not cause damage to tissues. In one non-limiting example, the metal is femoral or acetabular component used for hip repair. In another example, the metal is a fiber or other protuberance used in permanent attachment of a prosthesis to a patient. Other compositions, including ceramics, calcium compounds, such as, without limitation, aragonite, may be preferred, for example and without limitation, in repair of or re-shaping of skeletal or dental structures. Combinations of metal, ceramics and/or other materials also may prove useful. For instance, a metal femoral component of a hip replacement may comprise a ceramic ball and/or may comprise a plastic coating on the ball surface, as might an acetabular component.

In certain aspects, the composition is used for release of one or more therapeutic agents within a patient's body and/or incorporates one or more therapeutic agents. For example, at least one therapeutic agent is added to the composition described herein before it is implanted in the patient or otherwise administered to the patient, for example, a therapeutic agent is added to the described polyelectrolyte pair as they are combined. Generally, the therapeutic agents include any substance that can be coated on, embedded into, absorbed into, adsorbed to, or otherwise attached to or incorporated onto or into the composition or material described herein, or incorporated into a drug product that would provide a therapeutic benefit to a patient. Non-limiting examples of such therapeutic agents include antimicrobial agents, growth factors, emollients, retinoids, and topical steroids. Each therapeutic agent may be used alone or in combination with other therapeutic agents. For example and without limitation, a composition comprising neurotrophic agents or cells that express neurotrophic agents may be applied to a wound that is near a critical region of the central nervous system, such as the spine.

In certain non-limiting aspects, the therapeutic agent is a growth factor, such as a neurotrophic or angiogenic factor, which optionally may be prepared using recombinant techniques. Non-limiting examples of growth factors include basic fibroblast growth factor (bFGF), acidic fibroblast growth factor (aFGF), vascular endothelial growth factor (VEGF), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), transforming growth factors α and β (TGF-α and TGF-β), interleukin-8 (IL-8), granulocyte-macrophage colony stimulating factor (GM-CSF), interleukins, and interferons. Commercial preparations of various growth factors, including neurotrophic and angiogenic factors, are available from R & D Systems, Minneapolis, Minn.; Biovision, Inc, Mountain View, Calif.; ProSpec-Tany TechnoGene Ltd., Rehovot, Israel; and Cell Sciences®, Canton, Mass.

In certain non-limiting aspects, the therapeutic agent is an antimicrobial agent, such as, without limitation, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, Zn-pyrithione, and silver salts such as chloride, bromide, iodide and periodate.

In certain non-limiting aspects, the therapeutic agent is an anti-inflammatory agent, such as, without limitation, an NSAID, such as salicylic acid, indomethacin, sodium indomethacin trihydrate, salicylamide, naproxen, colchicine, fenoprofen, sulindac, diflunisal, diclofenac, indoprofen, sodium salicylamide; an anti-inflammatory cytokine; an anti-inflammatory protein; a steroidal anti-inflammatory agent; or an anti-clotting agents, such as heparin. Other drugs that may promote wound healing and/or tissue regeneration may also be included.

In certain non-limiting embodiments, cells are added to the composition. Non-limiting examples of useful cells include: stem cells, progenitor cells and differentiated cells; recombinant cells; muscle cells and precursors thereof; nerve cells and precursors thereof; mesenchymal progenitor or stem cells; bone cells or precursors thereof, such as osteoprogenitor cells, pre-adipocytes, etc.

Any useful cytokine, chemoattractant, drug or cells can be mixed into, mixed with, co-applied or otherwise combined with any composition as described herein. For example and without limitation, useful components include growth factors, interferons, interleukins, chemokines, monokines, hormones, angiogenic factors, drugs and antibiotics. Cells can be mixed into the composition or can be included on or within a substrate such as a biological scaffold, combined with the composition. In either case, when the substrate is seeded with cells, the cells can be grown and/or adapted to the niche created by incubation in a suitable medium in a bioreactor or incubator for a suitable time period to optimally/favorably prepare the composition for implantation in a patient. The substrate can be seeded with cells to facilitate in-growth, differentiation and/or adaptation of the cells. For example and without limitation, the cells can be autologous or allogeneic with respect to the patient to receive the composition/device comprising the gel. The cells can be stem cells or other progenitor cells, or differentiated cells.

As used herein, the terms "drug" and "drugs" refer to any compositions having a preventative or therapeutic effect, including and without limitation, antibiotics, peptides, hormones, organic molecules, vitamins, supplements, factors, proteins and chemoattractants.

As used herein, the terms "cell" and "cells" refer to any types of cells from any animal, such as, without limitation, rat, mice, monkey, and human. For example and without limitation, cells can be progenitor cells, such as stem cells, or differentiated cells, such as endothelial cells and smooth muscle cells. In certain embodiments, cells for medical procedures can be obtained from the patient for autologous procedures or from other donors for allogeneic procedures.

In a further aspect, a commercial kit is provided comprising a composition described herein. A kit comprises suitable packaging material and the composition. In one non-limiting embodiment, the kit comprises a liquid, gelled or dried ECM in a vessel, which may be the packaging, or which may be contained within packaging. The vessel may be a vial, syringe, tube or any other container suitable for storage and transfer in commercial distribution routes of the kit. Likewise, a product, such as a device, gel, scaffolding, suture, prosthetic, mesh, foam etc. including one or both of the soluble or structural compositions described herein may be packaged appropriately for commercial distribution.

According to one aspect of the invention, a method of production of aortic ECM is provided. The method uses a zwitterionic detergent, such as CHAPS or Betaines (any neutral compound having both positive and negative charges), and includes as a class detergents/surfactants such as 1-Dodecanoyl-sn-glycero-3-phosphocholine, 3-(4-tert-Butyl-1-pyridinio)-1-propanesulfonate, 3-(N,N-Dimethylalkylammonio)propane sulfonate, where alkyl is typically a linear, aliphatic hydrocarbon, such as a linear $C_{6-22}$ saturated hydrocarbon, 3-(1-Pyridinio)-1-propanesulfonate, Surfactin, and other, as are broadly-available from commercial sources, such as Sigma-Aldrich. Anionic detergents are any useful detergents comprising a negative charge, such as, without limitation, alkylbenzene sulfonates, bile acids such as deoxycholic acid, and organosulfates, such as SDS. Alternatives to Trypsin-EDTA are known, and other enzymes for cell detachment and tissue dissociation, as are available commercially, such as collagenase, hyaluronidase, elastase, papain, protease Type XIV, alone or in combination, optionally with Trypsin, for example from Sigma-Aldrich (e.g., Accutase®), and optionally chelating agents other than EDTA may be used to equal effect.

As a first step, fresh aortic tissue is obtained and fat and connective tissue is removed. Using any method, such as by use of forceps or scissors as described below, or by any automated mechanical process, the adventitial layer dissected from the medial layer to produce aortic adventitia.

The aortic adventitia is then frozen and thawed. Next, the material is incubated in a zwitterionic detergent and is typically washed. Washing is usually done using PBS and/or water, or other solvents, such as alcohol as is appropriate. The material is then incubated in a Trypsin-EDTA or an equivalent for dissociating cells and tissue, typically followed by washing. Next, the material is incubated in an anionic detergent, typically followed by washing. The material is subsequently disinfected, for example by treatment with peracetic acid, and is then washed. The material is then dried, e.g. by lyophilization, and is comminuted. In its dry state, the materials are optionally sterilized. The dry, comminuted material is rehydrated in an acid, such as HCl, ~pH<4.0, from 1 to 4, e.g. pH 1 to 2, for example 2.0±0.3, and is digested with an acid protease, such as pepsin, maintaining the pH of the solution at within the active range for the protease, e.g., <4.0, from 1 to 4, from 1 to 2, e.g., 2.0±0.3. Digestion may be partial or complete. Partial digestion may be accomplished by use of shortened acid protease digestion times, use of lower amounts of acid protease in the reaction, and/or by digestion above the optimal pH for the acid protease. Complete digestion is typically accomplished at an optimal pH for the acid protease, for example at pH of 2.5 or less, for example 2.0±0.3. To form a gel, the acidic solution is neutralized, e.g. to pH 6.8 to 7.8, to form a pre-gel solution, and the solution is incubated at a higher temperature, such as at room temperature (20° C.-25° C.) or 37° C. (e.g., from 20° to 50° C., from 30° to 45° C., from 35° to 42° C., or at 37° C.±5° C., 4° C., 3° C., 2° C., or 1° C.) to form a gel. Prior to, during or after gelation, the pre-gel solution can be sprayed, coated, mixed, layered, poured, injected or otherwise deposited on a substrate or into a substrate, such as a polymer, a ceramic, a metal, a tissue (ex vivo, or in vivo), a different devitalized tissue product, such as a sheet of SIS ECM, a non-woven material, a suture, or any other medically-useful material. In one aspect, the acid protease digestion is incomplete, but complete enough to produce a gel, leaving small particles of undigested ECM material within the resultant gel, which would be digested in situ during use of the composition—resulting in delayed release of therapeutic compositions thereof.

According to another aspect, a method of treating an aneurysm in a patient is provided, comprising administering to a surface of a blood vessel having an aneurysm, a devitalized, acid-protease-digested vascular adventitial, e.g., an aortic adventitial tissue, having a pH of from 6.8 to 7.8, for example prepared according to the method described herein. In one aspect, the blood vessel is the descending, abdominal, or ascending aorta, or aortic arch of the patient.

According to another aspect, a method of inducing vascularization or re-vascularization in a patient is provided. The method comprises administering to a living tissue, in vivo or ex vivo (e.g., in the case of a transplant) an acid protease-digested vascular adventitial, e.g. aortic adventitial ECM pre-gel or gel composition according to any aspect or embodiment provided herein, resulting in vascularization, e.g., revascularization, of the living tissue. In one aspect, the tissue is a wound in a patient, such as skin wound, for example and without limitation, a diabetic ulcer, such as a diabetic foot ulcer. In another aspect, the tissue is bone tissue, for example damaged bone tissue or bone tissue exhibiting osteoporosis. In another aspect, the tissue is myocardium and/or vasculature thereof in a patient, for example a wound or an infarct in a patient's myocardium.

EXAMPLES

Free rupture or dissection of the ascending aorta is a concerning clinical problem that occurs in up to 2.5 million patients per year worldwide. Such aortic catastrophe is often fatal, can occur without warning, and the only treatment option is emergent aortic replacement. A solution to this problem is offered by an aorta-derived extracellular matrix hydrogel as a prophylactic and minimally-invasive treatment option for patients at risk for aortic rupture. This goal is bolstered by active hypothesis-driven research defining what mechanisms cause endothelial dysfunction in the setting of human aortic disease and how matrix-driven signaling impacts vasculogenesis by local progenitor cells in the adventitia, the outer layer of the aortic wall. This new knowledge drives the development of a regenerative medicine approach to invoke remodeling of the aortic wall itself, essentially repairing the aorta from the outside-in through regeneration of the associated microvascular network.

Example 1—Preparation of Adventitial Hydrogel

To study the influence of the adventitial extracellular matrix (ECM) on vasa vasorum function, hydrogels were developed from decellularized human and porcine aortic adventitia. Porcine aortic specimens were obtained from commercial sources, while human aorta was harvested during open aortic replacement operations with IRB approval and informed patient consent. The adventitia was delaminated from the medial layer and incubated in a zwitterionic detergent (8 mM CHAPS, 1M NaCl, and 25 mM EDTA) for 24 hr at 37° C., followed by washing in PBS then in deionized water for 2 hr. The adventitia was then submerged in an anionic detergent (0.5% SDS, 1M NaCl, and 25 mM EDTA) for 24 hr, and 2 hours in deionized water, followed by lyophilization, exposure to 70% ethanol and rinsed with deionized water and PBS to rehydrate the ECM. Complete decellularization of aortic tissue was confirmed by absence of DAPI staining in paraffin-embedded sections. Following lyophilization and grinding, ECM powder was digested in 0.01 N HCL and pepsin for 24 hr. Western blotting analysis revealed that ECM digests contain elastin and type I collagen (see, FIG. 1). Hydrogel films were formed from neutralized ECM digests. Gelation kinetic analyses demonstrated that peak gelation was reached within 90 minutes of incubation in a 37° C. dry heat incubator. Scanning electron microscopy revealed that hydrogel films exhibit native ECM fiber-like microarchitecture. Aortic ECM hydrogels may serve as cell culture substrates to study matrix-derived mechanisms of microvascular dysfunction in the setting of aneurysm. The clinical translation of this work is that aortic ECM hydrogels might function as native biologic materials for tissue regeneration in cardiovascular applications.

Figure 2:
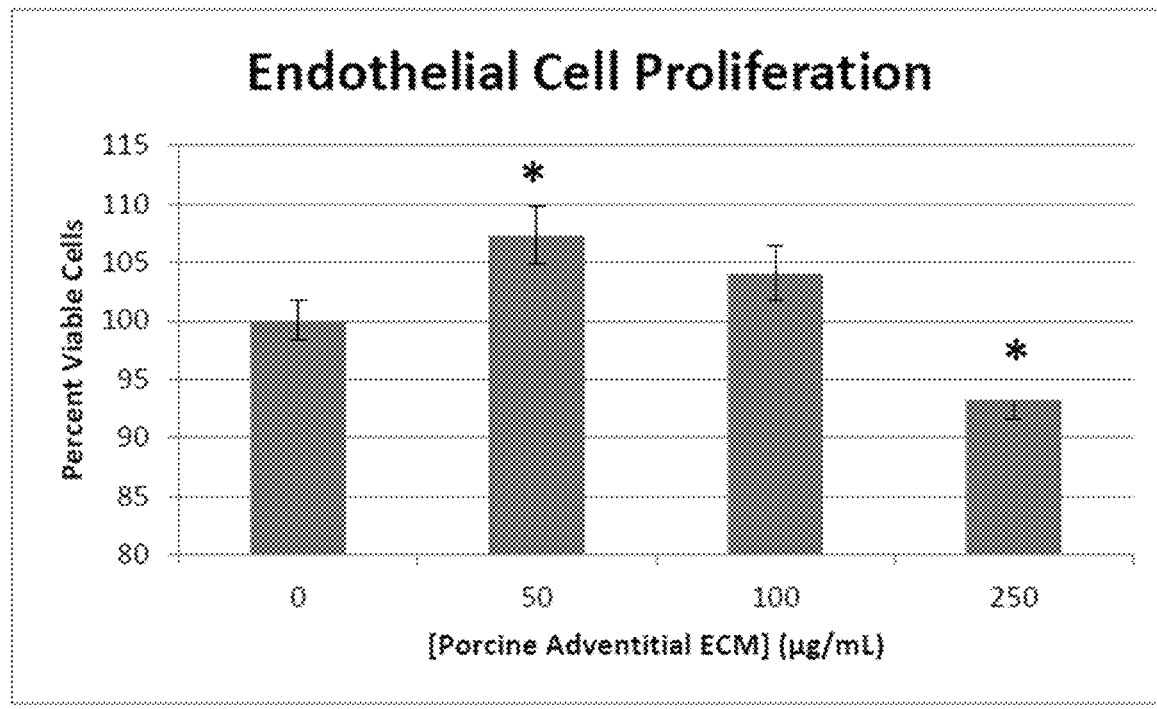
FIG. 2: Human endothelial cell proliferation. Cells were cultured for 12 hr in the presence or absence of 50, 100 and 250 µg/mL porcine adventitial ECM digest. Cell proliferation was measured using an MTT ([3-(4,5-dimethylthiazol-2-yl)-2,5-diphenyltetrazolium bromide])-based assay. * Significant from cells cultured in basal medium conditions alone (0 µg/mL pAdvECM), p<0.05.

Porcine aortic adventitia was decellularized and digested as described above. Human endothelial cells (P16) were seeded at a density of $5 \times 10^3$ cells/cm$^2$ and cultured in the presence of 0-250 µg/mL porcine adventitial ECM digest (pAdvECM) for 12 hours at 37° C. in a humidified incubator. Cell proliferation was measured using an MTT conversion assay (Cell Titer, Promega) according the manufacturer's instructions. As shown in FIG. 2, 50 µg/mL pAdvECM digest increased human endothelial cell proliferation ($p<0.05$) compared to endothelial cells cultured in basal growth medium alone (endothelial growth medium, Cell Applications). Whereas, higher doses of pAdvECM digest (250 µg/mL) decreased cell proliferation ($p<0.05$). This noted decrease in cell proliferation by higher doses of ECM digest may be related to the acidic pH of the culture medium evidence by a noted color change in the phenol-red containing medium upon addition (data not shown). These data provide preliminary evidence that decellularized pAdvECM digests exhibit mitogenic bioactivity and can invoke endothelial cell proliferation, a necessary mechanism for vasculogenesis.

Figure 3:
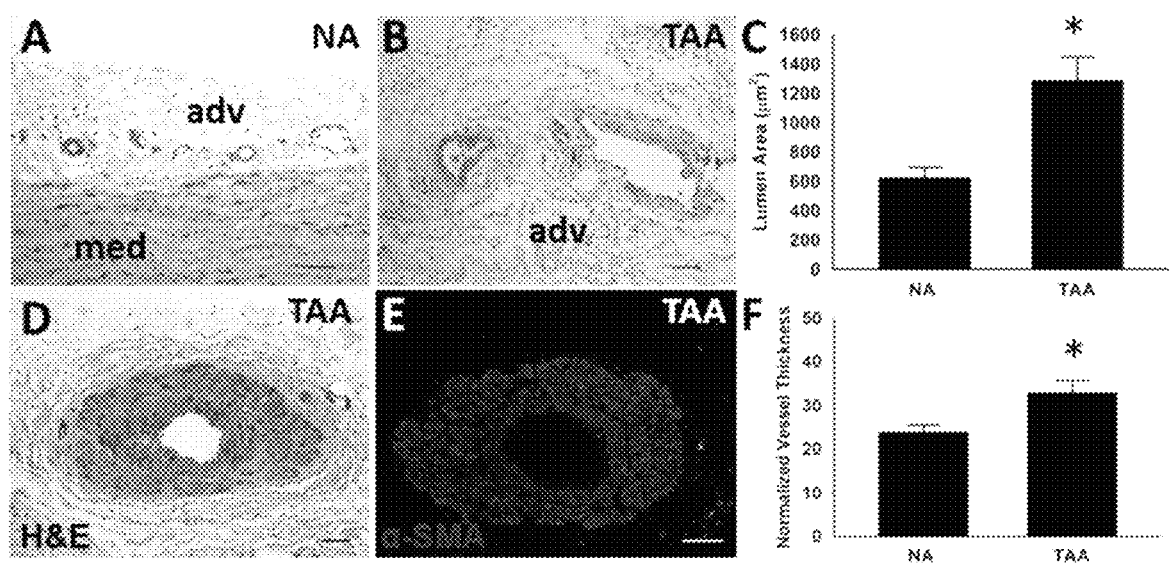
FIG. 3. Microvascular remodeling, or pathological increase in luminal diameter and vessel wall thickness, is associated with aneurysm in human aorta. Histological evidence of increased luminal diameter in thoracic aortic aneurysm (TAA, B) vs. Non-aneurysmal (NA, A, C) and increased wall thickness (D-F). Scale bar=100 µm.

Example 2—Microvascular Remodeling in the Aorta is Associated with Thoracic Aortic Disease Research revealed microvascular remodeling associated with aneurysm in the ascending thoracic aorta. Note the paucity of microvessels in specimens of aneurysmal aorta, along with increased luminal area of existing vessels and wall thickening (FIG. 3). Also, that the human aortic adventitia is home to a progenitor cell niche, including endothelial and pericyte progenitor cells, the precursors of microvasculature networks. This new knowledge inspires a regenerative medicine approach as a minimally-invasive treatment strategy for patients at risk for aortic rupture by harnessing local progenitor cells for therapeutic microvascular regeneration. Decellularized aortic extracellular matrices (ECMs) described herein are proposed for use as stimuli for therapeutic microvascular regeneration.

Figure 4:
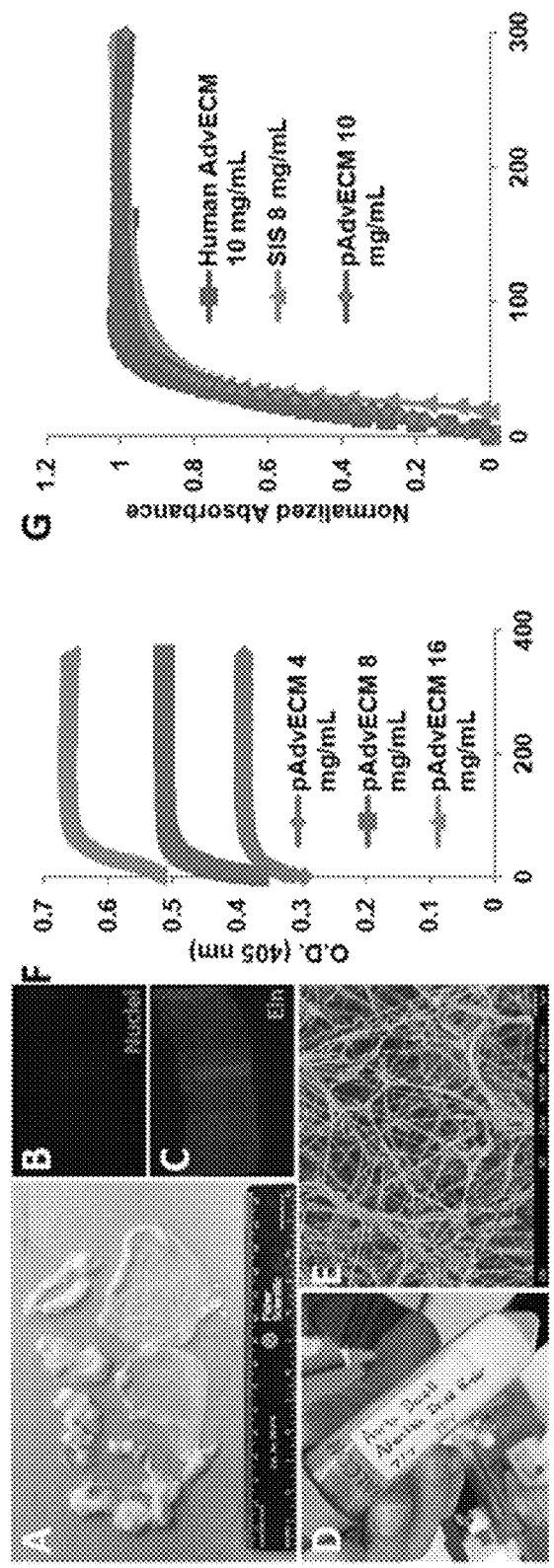
FIG. 4. Aortic ECM. A) Decellularized porcine aorta. B) Aortic cross-section revealing complete removal of cell nuclei (DAPI, blue) amidst intact elastic layers (C, Autofluoresence, green). D) Lyophilized powdered ECM. E) Scanning electron micrograph of 10 mg/mL adventitial hydrogel film revealing a fibrous microstructure, scale bar=1 µm. F) Optical density (O.D.) of ECM gels over time. G) Rate of gelation for porcine and human vascular ECMs on par with other ECMs (porcine sub-intestinal submucosa (SIS)). Lines represent and normalized O.D. readings as a measure of gel formation over time.
Figure 5:
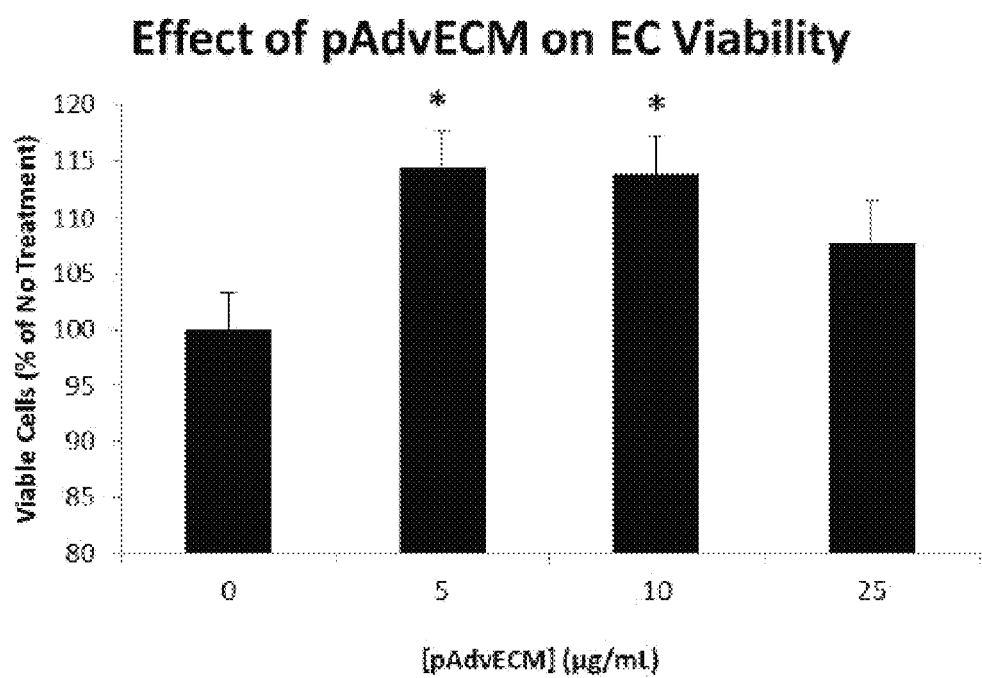
FIG. 5: Human endothelial cell proliferation. Cells were cultured for 18 hr in the presence or absence of 5, 10, 25, 50, 100 and 250 µg/mL pAdvECM. Cell proliferation was measured using an MTT-based assay. * Significant from cells cultured in basal medium conditions alone (0 µg/mL pAdvECM), p<0.02. Results displayed are representative of three independent experiments with two different batches of pAdvECM.
Figure 6:
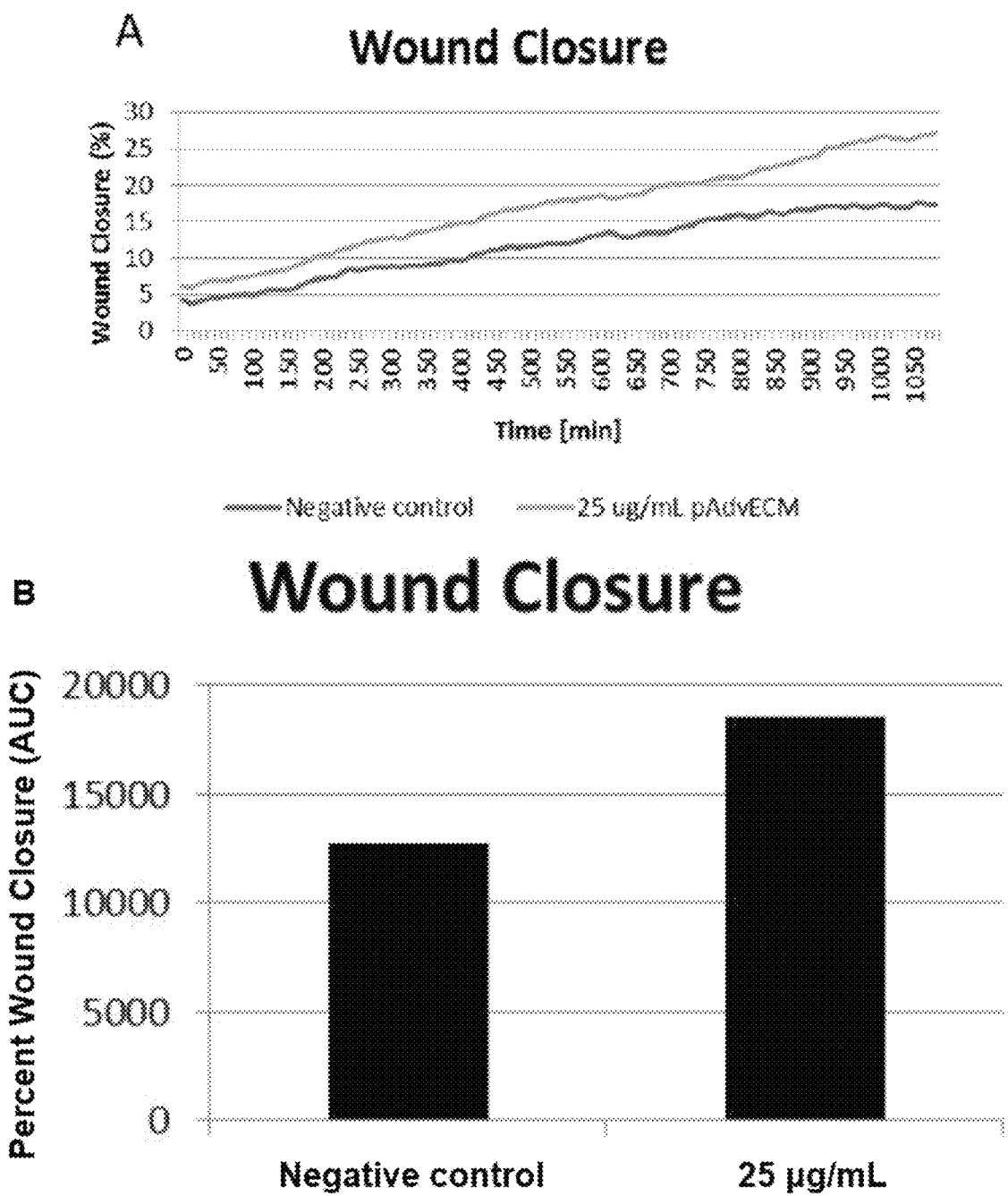
FIG. 6. Endothelial cell migration. A) Wounded cell monolayers cultured in the presence of pAdvECM demonstrated increased wound closure over 18 hr when compared with untreated cells cultured in their basal growth medium. B) Area under the curves (AUC) in (A).
Figure 7:
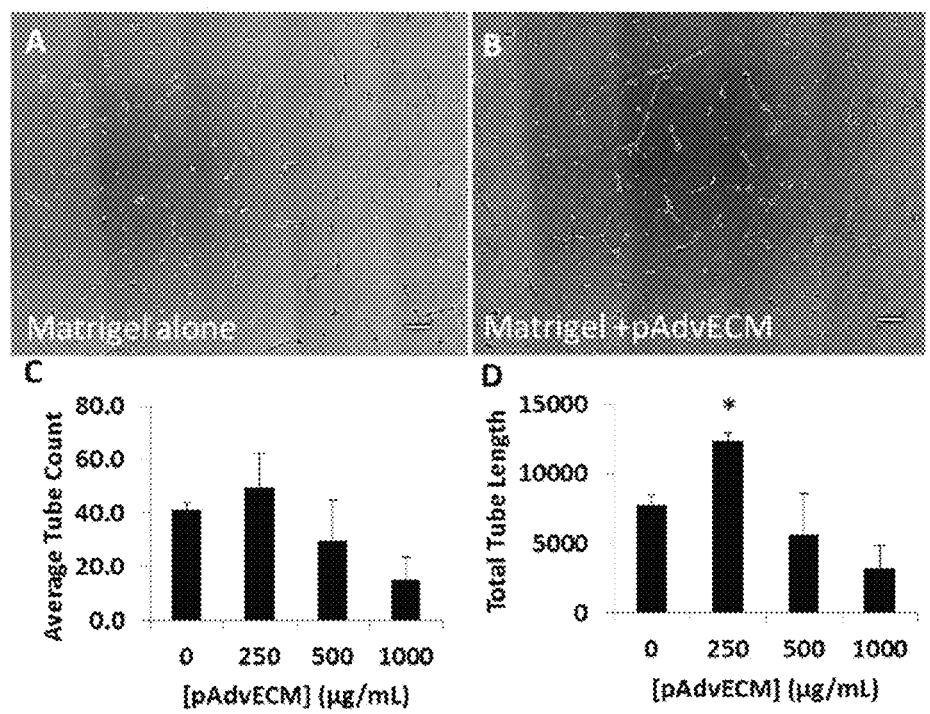
FIG. 7. Endothelial cell branching in vitro. Human endothelial cells (12.5×104) were seeded on pAdvECM-spiked growth factor-reduced Matrigel substrates and cultured for up to 18 hr. Cells cultured on Matrigel alone (A) formed tube-like structures of relatively short length while pAdvECM-spiked Matrigel increased the length of tube-like structures (B, D). Number of tube-like structures was unchanged among cells cultured on pAdvECM-treated and non-treated Matrigel substrates. *p<0.03, n=3.

The vascular ECM hydrogel described herein is unique in both method and composition (FIG. 4). Following decellularization of mammalian vascular ECM (FIG. 4(A-C)), digestion of the lyophilized and morcellated ECM (FIG. 4(D)) deviates substantially from Freytes, D. O., et al. ((2008). "Preparation and rheological characterization of a gel form of the porcine urinary bladder matrix." Biomaterials 29(11): 1630-1637) in that pH is closely monitored and tightly controlled to pH 2.0±0.3. Cell-friendly ECMs from porcine and human aorta have been optimized for hydrogel formation with fibrous microarchitecture similar to native ECM (FIG. 4(E)). Preliminary experiments demonstrate that vascular ECM hydrogels reach peak gelation within 90 minutes in a dry heat incubator at 37° C. (FIG. 4(F)) with rates of gelation for both porcine and human aortic ECMs being similar to that of porcine sub-intestinal sub-mucosa (SIS) (FIG. 4(G)) and urinary bladder matrix. (Freytes et al. 2008).

Example 3—Evaluation of Vascular ECM Bioactivities

Demonstrating the therapeutic potential of vascular-derived extracellular matrices (ECMs) involves evaluating their bioactivity as regulators of 1) cell proliferation 2) cell migration and 3) endothelial branching. A series of experiments were performed to address the above three functions.

Adventitia-derived ECM is mitogenic. Porcine aortic adventitia was decellularized and digested as previously described above to obtain extracellular matrix (pAdvECM). Human endothelial cells (P16-18) were seeded at a density of $5\times10^3$ cells/cm$^2$ and cultured in the presence of 0-25 µg/mL porcine adventitial ECM digest (pAdvECM) for 2-18 hours at 37° C. in a humidified incubator. Cell proliferation was measured using an MTT conversion assay (Cell Titer, Promega) according the manufacturer's instructions. From the data shown in FIG. 5, 5-10 µg/mL pAdvECM digest increased human endothelial cell proliferation (p<0.02) compared to endothelial cells cultured in basal growth medium alone (endothelial growth medium, Cell Applications). These data provide preliminary evidence that decellularized pAdvECM digests exhibit mitogenic bioactivity and can invoke endothelial cell proliferation, an important mechanism for vasculogenesis.

Adventitial-derived ECM stimulates endothelial cell migration. The effect of pAdvECM digest on endothelial cell migration was evaluated using an in vitro wound healing or "scratch test" pilot assay. In brief, a scratch "wound" was made using a P20 pipet tip in monolayer cultures of human endothelial cells at confluence, followed by culture in the presence or absence of 25 µg/mL pAdvECM for up to 18 hr. Cells were placed within a stage-top incubation chamber and maintained at 37° C., 5% $CO_2$ and humidity. Images were obtained using phase-contrast light microscopy on an inverted TE-2000 microscope (Nikon) every 10 minutes. Percent of wound closure over time was calculated from images by creating binary thresholds using image analysis software (NIS Elements 4.2, Nikon). We conclude from the data shown in FIG. 6 that treatment of endothelial cells with pAdvECM increased the rate of cell migration, evidenced by the increased percentage of wound closure when compared with cells in their basal culture medium (negative control).

Adventitial-derived ECM enhanced endothelial cell branching. The effect of pAdvECM on endothelial cell branching was evaluated in vitro. Briefly, 0, 250, 500 or 1000 µg/mL of pAdvECM was combined with growth factor reduced-Matrigel™ (Corning) and used to coat the surface of wells in a 48-well tissue culture plate. The pAdvECM/Matrigel mixture (150 µL) was allowed to cure for 1 hr at 37° C. prior to seeding of 12.5×104 cells/well in endothelial growth medium. We conclude from the data shown in FIG. 7, that pAdvECM enhanced endothelial cell branching on Matrigel substrates when compared with Matrigel alone (p<0.03). While number of tube-like structures was unchanged with pAdvECM treatment, their length was found to be increased when compared with untreated cells cultured on Matrigel substrate alone.

Example 4—Clinical Translation

Figure 8:
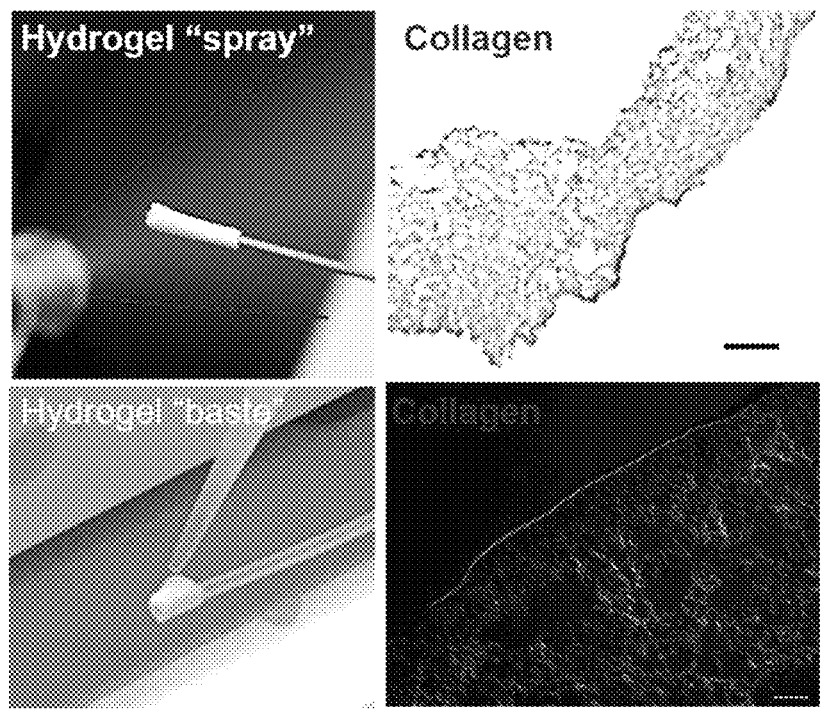
FIG. 8. Photographs and photomicrographs of two methods of deposition of the hydrogel materials described herein as described in Example 4.
Figure 9:
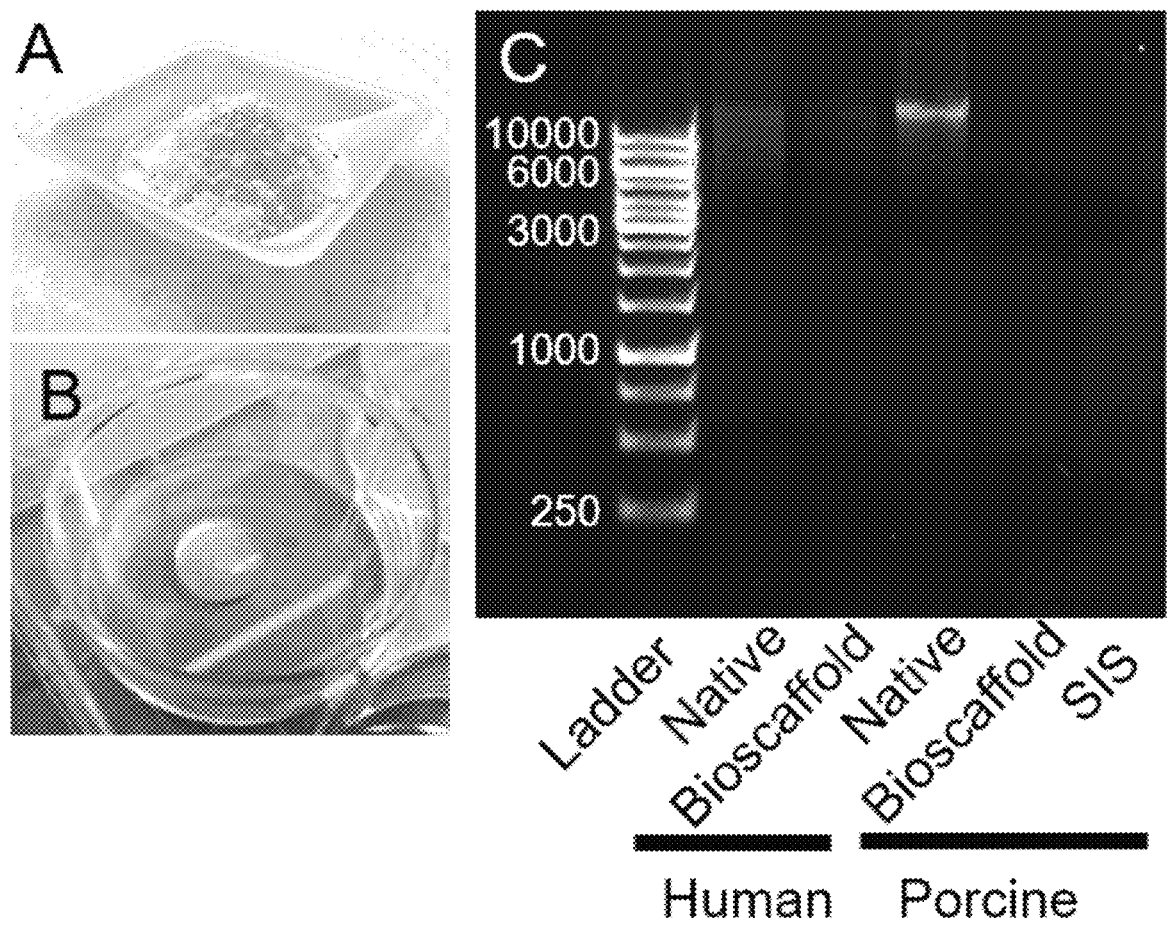
FIG. 9. Preparation and characterization of pAdvECM bioscaffolds. A) pAdvECM bioscaffold as a lyophilized ground powder. B) Hydrogel formation from pH-neutralized pepsin-digested pAdvECM bioscaffolds after 1 hr at 37° C. C) DNA extracts from 1.2 mg total tissue weight were qualitatively analyzed using ethidium bromide-containing agarose gel electrophoresis. pAdvECM Bioscaffold and SIS groups showed marked reduction of DNA content compared to native aortic tissue.

Therapeutic efficacy of the hydrogel will be tested using this spraying device in pre-clinical models in small (mouse: sub-cutaneous vascularization) and large (rabbit and porcine: aneurysm) animals. Hydrogels can be aerosolized for minimally-invasive delivery. An ECM hydrogel can be sprayed or basted onto a polyurethane-base tubular scaffold. Sprayed ECM hydrogel was found to be dispersed within the wall of the tubular scaffold, or as an outer sheath by simply "basting" the gel onto the outer surface of the tubular scaffold as detected using a picrosirius red stain for collagen with and without polarized light (FIG. 8). This work is a vertical leap in the field by delivering biologic materials to the aorta to harness local perivascular progenitor cells that are capable of therapeutic vasculogenesis-shifting focus to a minimally-invasive treatment approach to invoke aortic regeneration in the setting of aneurysm using aerosolized biological hydrogels.

Example 5—Preparation of Aortic ECM-Derived Hydrogels

The following is an exemplary and non-limiting protocol for preparation of aortic ECM-derived hydrogels.

Solutions. Zwitterionic Detergent: 5.895 g CHAPS (3-[(3-Cholamidopropyl) dimethylammonio]-1-propanesulfonate) (8 mM); 70.08 g NaCl (1 M); 8.76 g EDTA (25 mM); and 1200 mL PBS. Trypsin-EDTA: 1.2 g Trypsin (0.1%); 0.456 g EDTA (1×); and 1200 mL PBS. Anionic Detergent: 70.08 g NaCl (1M); 8.76 g EDTA (25 mM); 6.228 g SDS (18 mM); and 1200 mL PBS. Peracetic Acid: 7.98 mL Peracetic Acid stock (PAA, 0.1%); 1152 mL distilled water (dH$_2$O, 96%); and 48 mL 100% Ethanol (4%). 0.01 N Hydrochloric Acid: 50 µL 12 N HCl stock; and 9.95 mL dH$_2$O. 5 N Hydrochloric Acid: 4.167 mL 12 N HCl solution; and 5.833 mL dH$_2$O.

Procedure 1: Cleaning of Fresh Aortic Tissue and Isolation of Adventitial Layer. Using blunt forceps and scissors, remove all extraneous fat and connective tissue from fresh or frozen porcine or human aorta. Ensure tissue does not dry out by hydrating tissue occasionally with dH$_2$O. Using blunt forceps, delaminate the adventitial layer from the medial layer of aortic specimens to create sheets of aortic adventitia. Delaminated aortic adventitia is cut into ~2.5×2.5 inch squares for decellularization. Remove 1 square from the middle and corner of a fresh (not decellularized) section of fresh aorta, both to be snap frozen; 1 for histological analysis, the other for future studies. To measure total wet weight of aortic adventitial squares, gently dab tissue dry and weigh on precision balance. The following protocol is optimized for approximately 30 g of adventitial sheet squares (wet weight). Freshly isolated tissue must be frozen at −80° C. at least overnight and allowed to thaw before processing.

Procedure 2: Decellularization. Place adventitial tissue in 1 L flask and fill with 800 mL DI water. Place 1 L flask with adventitia on orbital shaker and run at 300 rpm for 30 minutes. Remove D.I water and replace with fresh D.I water (800 mL for adventitia). Repeat three more times (4 total rinses, 2 hour duration on shaker). While tissue is on shaker begin prep of Zwitterionic Detergent. Place Zwitterionic detergent in 37° C. water bath 30 minutes prior to completion of tissue shaking (ensures solution is at appropriate temperature for next step). Upon completion of shaking remove and discard D.I water. Transfer each tissue type to a separate 1-L flask. Fill adventitial flask with 400 mL of warm Zwitterionic Detergent (400 mL per approx 30 g of tissue). Place flasks in 37° C. shaking water bath. Let flasks sit in rocking bath for 12 hours. After 12 hours in bath replace Zwitterionic detergent. For replacement follow identical procedure as initial Zwitterionic detergent prep. After replacing Zwitterionic detergent replace flasks in warm shaking water bath and allow incubation for another 12 hours (24 hours of total Zwitterionic incubation). 30 minutes before completion of incubation bring 2400 mL of 1×PBS up to 37° C. After incubation completion remove flasks from shaking water bath and properly discard Zwitterionic detergent. Rinse tissues with 37° C.—1×PBS on rocking water bath for 15 minutes (400 mL for adventitia). Replace 1×PBS and rinse on rocking water bath for 15 more minutes (30 min total). Store tissue overnight at 4° C. in still dH$_2$O. Transfer tissues to clean flasks with 400 mL dH$_2$O. Using the orbital shaker (300 rpm) shake the tissue for 1 hour. Replace dH$_2$O and shake for additional hour (2 hours total). 30 minutes before conclusion of dH$_2$O shake, prep Trypsin-EDTA solution and bring up to 37° C. Empty and discard spent dH$_2$O water. Replace with 400 mL Trypsin-EDTA solution. Incubate tissue in shaking water bath for 30 minutes at 37° C. Replace Trypsin-EDTA solution with second batch of solution and incubate for 30 more minutes in 37° C. shaking water bath (1 hour total). Dispose of Trypsin-EDTA solution. Either clean or use new 1 L flasks. Transfer tissues to new flasks. Fill flasks with 400 mL dH$_2$O. Shake flasks on orbital shaker at 300 rpm for 1 hour. Replace dH$_2$O and shake for additional hour (2 hours total). 30 minutes prior to finishing dH$_2$O rinse, begin prep of Anionic Detergent. Warm anionic detergent to 37° C. Discard spent dH$_2$O and replace with 400 mL Anionic Detergent). Place flasks in 37° C. shaking water bath for 12 hours. Repeat anionic detergent incubation. Properly dispose of Anionic Detergent. Either clean or obtain new 1 L flasks. Fill flasks with 400 mL 1×PBS. Shake tissue and PBS solution on orbital shaker at 300 rpm for 15 minutes. Discard spent PBS. Repeat PBS wash. Store tissue overnight at 4° C. in still dH$_2$O. Transfer tissues to clean flasks with 400 mL of dH$_2$O. Using the orbital shaker (300 rpm) shake the tissue for 7 hours. Replace dH$_2$O and shake for additional 7 hours (14 hours total). Empty dH$_2$O and fill flasks with prepped Peracetic acid solution (400 mL). Shake flasks on orbital shaker for 2 hours at 300 rpm. Properly dispose of Peracetic acid. Clean or obtain new 1 L flasks. Fill flasks with 1×PBS (400 mL). Shake tissue on orbital shaker (300 rpm) for 15 min. Discard spent PBS and fill flasks with dH$_2$O (400 mL). Shake tissue and dH$_2$O on orbital shaker at 300 rpm for 15 minutes. Replace dH$_2$O and shake for additional 15 min (30 total). Discard dH$_2$O and fill with PBS (400 mL). 57. Shake on orbital shaker for 15 minutes at 300 rpm. Expand samples on aluminum foil. Remove two 0.5×0.5 cm$^2$ sections from the middle and corner of 3 total decellularized square sections for quality control to confirm decellularization. From each decellularized square sampled, snap freeze 1 section for histological sectioning and 1 stored in a microfuge tube for future assays. Wrap samples with aluminum foil and crimp edges. Freeze in −80° C. overnight. Transfer frozen samples to lyophilizer, and initiate vacuum. Check samples after 2 days by handling: fully lyophilized samples will be brittle, with little to no flexibility. If not "brittle" by 2 days, lyophilize for an additional day and follow-up after 24 hours to see if "brittle" tissue achieved. Once tissue observed to be brittle, prep decellularized, lyophilized, brittle samples by breaking squares into 0.5-0.75×0.5-0.75 cm$^2$ pieces to facilitate tissue grinding.

Procedure 3: Grinding of Lyophilized Adventitia. Assemble grinder with 60 mesh screen to collect finely ground adventitial powder. Add decellularized, lyophilized adventitial pieces gradually to hopper on grinder, forcing tissue through with wooden dowel. Once all tissue is ground, collect powder and store at room temperature in a labeled, air-tight, sealed container.

Procedure 4: Adventitial Powder Digestion. Weigh out 0.5 g of lyophilized, ground adventitia powder using a precision balance. Weigh out 100 mg of pepsin (Sigma) using a precision balance. Add 45 μL 5 N HCl. Confirm resulting pH 2 using acidic pH paper and matching to the pH 2 shade of red. Slowly add pepsin to stirring pH 2, 0.01 N HCl solution. 5. Once pepsin is solubilized in 0.01 HCl, gradually add all adventitial powder to stirring pepsin-HCl solution. After all adventitial powder added to solution, note the start time of digestion. Check and confirm pH of 2 at start of digestion. Allow to continue stirring at 900 RPM for 1.5 hours. While still stirring at 900 RPM, after 1.5 hours of digestion, check pH of "digest". If pH is between 2-3, add 120 μL of 5 N HCl. Confirm pH adjustment to 2 by matching to pH 2 on pH paper. Continue to check pH of solution every 30 minutes for 1.5 hours, adding 20 μL 5 N HCl to the solution if pH is observed between 2-3. Continue stirring at 900 RPM for 15 hours. After 15 hours, increase stir of digest to 1100 RPM to compensate for increased viscosity. Confirm pH is still 2. Continue stirring for remaining 6 hours of 24 hour digest cycle. After 24 hours of digestion, decrease RPM to 200 RPM to allow bubbles to rise out of digest to surface of solution for 10 minutes. After 10 minutes at 200 RPM, store ECM digest in 500 μL aliquots at −20° C. or transfer to ice and prepare hydrogels as below.

Procedure 5: Hydrogel Formation. Keep, or thaw previously-frozen ECM digest on ice. Keep all reagents on ice: 10×PBS, 0.1 N NaOH, 1 N NaOH, 1 N HCl. Mix in the following order: 1 part 10×PBS, 1 part 0.1 NaOH and 8 parts ECM digest. Vortex to mix. Check pH and adjust to 6.8-7.8. Add hydrogel to tissue culture wells, coverglass or molds and incubate for 60-90 minutes in a 37° C. dry heat incubator, overnight in a humidified 37° C. incubator or up to 8 hr at room temperature.

Example 6—Perivascular Extracellular Matrix Hydrogels Mimic Native Matrix Microarchitecture and Promote Angiogenesis Via Basic Fibroblast Growth Factor Extracellular matrix (ECM)-derived bioscaffolds have been shown to elicit tissue repair through retention of bioactive signals. Given that the adventitia of large blood vessels is a richly vascularized microenvironment, we hypothesized that perivascular ECM contains bioactive signals that influence cells of blood vessel lineages. ECM bioscaffolds were derived from decellularized human and porcine aortic adventitia (hAdv and pAdv, respectively) and then shown have minimal DNA content and retain elastin and collagen proteins. Hydrogel formulations of hAdv and pAdv ECM bioscaffolds exhibited gelation kinetics similar to ECM hydrogels derived from porcine small intestinal submucosa (pSIS). hAdv and pAdv ECM hydrogels displayed thinner, less undulated, and fibrous microarchitecture reminiscent of native adventitia, with slight differences in ultrastructure visible in comparison to pSIS ECM hydrogels. Pepsin-digested pAdv and pSIS ECM bio scaffolds increased proliferation of human adventitia-derived endothelial cells and this effect was mediated in part by basic fibroblast growth factor (FGF2). Human endothelial cells cultured on Matrigel substrates formed more numerous and longer tube-like structures when supplemented with pAdv ECM bioscaffolds, and FGF2 mediated this matrix signaling. ECM bioscaffolds derived from pAdv promoted FGF2-dependent in vivo angiogenesis in the chick chorioallantoic membrane model. Using an angiogenesis-focused protein array, we detected 55 angiogenesis-related proteins, including FGF2 in hAdv, pAdv and pSIS ECMs. Interestingly, 19 of these factors were less abundant in ECMs bioscaffolds derived from aneurysmal specimens of human aorta when compared with non-aneurysmal (normal) specimens. This study reveals that Adv ECM hydrogels recapitulate matrix fiber microarchitecture of native adventitia, and retain angiogenesis-related factors and bioactive properties such as FGF2 signaling capable of influencing processes important for angiogenesis. This work supports the use of Adv ECM bioscaffolds for both discovery biology and potential translation towards microvascular regeneration in clinical applications.

The potential for ECM bioscaffolds to invoke angiogenesis is of particular importance for regenerative medicine applications. Although the vasculogenic and angiogenic mechanisms of ECM bioscaffolds are not fully understood, gradual release of growth factors during ECM degradation is a likely mechanism of action. Since immobilized growth factors secreted by the resident cells fortify ECM, vascular ECM is a viable candidate biomaterial for invoking vasculogenesis and angiogenesis. The adventitia of blood vessels is a perivascular microenvironment that is heterogeneous in both form and function. Not only does the adventitia provide the majority of biomechanical strength to the vessel by nature of the woven network of fibrous proteins of the ECM, but it also serves as a progenitor cell niche. Furthermore, the diversity of cell composition in the vascular adventitia renders this ECM microenvironment a prime candidate for a multitude of desirable bioactive effects on blood vessel cell populations. Understanding the role of the adventitial ECM in vascular physiology will provide insight into cardiovascular disease particularly by exploring ECM bioscaffolds derived from human adventitia. Porcine adventitial ECM (pAdv) bioscaffolds, with their greater availability, can be utilized to harness their intrinsic bioactivity to develop potentially regenerative therapeutics.

This study tested the hypothesis that perivascular ECM contains bioactive signals that influence cells of blood vessel lineages. The composition and gelation kinetics of ECM hydrogel biomaterials formulated from human and porcine decellularized aortic adventitia was characterized, and the signaling activity of porcine ECM bioscaffolds in processes related to angiogenesis was evaluated using primary adventitia-derived human endothelial cell culture models, tube-forming in vitro assays, and an in vivo angiogenesis model. Porcine small intestinal submucosa (pSIS) was chosen as a control ECM due to its prior thorough characterization and current utilization as a clinically-relevant bioscaffold. The findings below reveal several biomimetic features of perivascular ECM that may render these natural biomaterials useful for discovery biology and show promise for regenerative medicine applications.

Materials and Methods

Tissue Collection. Human ascending thoracic aorta specimens (n=40 patients) were collected during ascending aortic replacement operations or heart transplants with informed patient consent and approval of the institutional review board or from organ donors via the Center for Organ Recovery and Education. Acquisition of all human specimens was in accordance with the Helsinki Declaration of 1975, as revised in 1983. Following excision, tissue specimens were placed in saline on ice and transported to the laboratory. Specimens were collected from 22 males and 18 females ranging in age from 17 to 82 years. Porcine ascending aortic specimens were obtained from a commercial source (Tissue Source, Lafayette, Ind.) and shipped on wet ice. Porcine SIS specimens were obtained from a local abattoir (Thoma Meat Market, Saxonburg, Pa.) and prepared as previously described. Upon acquisition in the laboratory, all specimens were promptly stored at −80° C. until use.

Decellularization of Aortic Adventitia. Adventitial ECM bioscaffolds were prepared from decellularized aortic tissue specimens from 39 patients and two pigs. The adventitial layer was delaminated from the media and decellularized using a previously established method (Reing J E, et al. The effects of processing methods upon mechanical and biologic properties of porcine dermal extracellular matrix scaffolds. Biomaterials. 2010; 31:8626-33). Briefly, the adventitial specimens were incubated in a solution of 8 mM CHAPS (3-[(3-cholamidopropyl) dimethylammonio]-1-propanesulfonate, Thermo Fisher Scientific, Waltham, Mass.), 1M NaCl (Thermo Fisher Scientific), and 25 mM EDTA (ethylenediaminetetracetic acid, Thermo Fisher Scientific) for 24 hr at 37° C., followed by washing in 1×PBS (phosphate buffered saline, Thermo Fisher Scientific) then in deionized water (dH$_2$O). The tissue was then placed on a shaker for 1 hour in a solution containing 0.1% trypsin (Amresco, LLC, Solon, Ohio) and 0.04% EDTA, rinsed in dH$_2$O, then shaken in a solution of 0.5% SDS (sodium dodecyl sulfate, Thermo Fisher Scientific), 1M NaCl, and 25 mM EDTA for 24 hr, followed by washing in 1×PBS and dH$_2$O. The tissue was then placed on a shaker in a solution of 0.1% peracetic acid (Rochester Midland Corporation, Rochester, N.Y.) and 4% ethanol, followed by rinsing with 1×PBS and dH$_2$O before freezing overnight at −80° C. and lyophilizing. Decellularized aortic adventitia from human and porcine aorta (here on referred to as hAdv and pAdv ECM bioscaffolds) was lyophilized and finely ground to produce an ECM bioscaffold powder for further enzymatic digestion. SIS ECM bioscaffold was prepared previously as described elsewhere (Badylak S F, et al. Small Intestinal Submucosa as a Large Diameter Vascular Graft in the Dog. Journal of Surgical Research. 1989; 47:74-80. Powdering and gelation of SIS utilized the same procedures described in this report.

Qualitative and Quantitative Assessment of DNA Content. Remnant DNA content was quantified from 25 mg of powdered Adv ECM bioscaffolds from porcine (2 pigs, pooled) and human aorta (4 patient specimens, pooled) using the QIAamp DNA Mini Kit (QIAgen, Germantown, Md.) according to the manufacturer's instructions. Final elution volume was 50 μL Buffer AE. Qubit 2.0 (Thermo Fisher Scientific) was utilized to quantify the concentration of dsDNA in each extract. DNA extracts from 1.2 mg dry tissue weight of powdered ECM bioscaffolds and extracts from 1.2 mg wet tissue weight from native aorta were electrophoresed on a 1% agarose (Thermo Fisher Scientific) gel containing 0.003% (v/v) ethidium bromide (Sigma Life Science, St. Louis, Mo.) and visualized under UV light on a Chemidoc XRS Bioimaging Station (Bio-Rad, Hercules, Calif.).

Digestion of Powdered ECM Bioscaffolds. Adv and pSIS ECM bioscaffold powders were digested at a concentration of 20 mg/mL by stirring at 1600 RPM at room temperature for 24 hr in a 0.01 N hydrochloric acid solution (pH 2, Thermo Fisher Scientific) containing 1 mg/mL pepsin from porcine gastric mucosa (2000-2300 U/mg, Sigma). After 24 hr, the ECM digests were either immediately used for gelation kinetics assays or stored at −20° C. for future use.

Detection of Collagen and Elastin Content. Pepsin-soluble collagen was extracted from native adventitia and from adventitia-derived ECM bioscaffold powder using 0.1 mg/mL pepsin in 0.5M acetic acid overnight at 4° C. After isolation and concentration steps, the amount of pepsin-soluble collagen was determined in each sample as previously described (Phillippi J A, et al. Mechanism of aortic medial matrix remodeling is distinct in patients with bicuspid aortic valve. J Thorac Cardiovasc Surg. 2014; 147:1056-64) [38] using the Sircol Soluble Collagen assay (Biocolor Ltd, UK), according to the manufacturer's instructions. The amount of pepsin-soluble collagen determined in each extract was normalized to weight of wet tissue or weight of Adv ECM bioscaffold powder.

The amount of α-elastin was determined as described before (Phillippi J A, et al. J Thorac Cardiovasc Surg. 2014; 147:1056-64) using the Fastin Elastin assay (Biocolor), according to the manufacturer's protocol. Insoluble elastin was converted to water soluble α-elastin by subjecting native adventitia and Adv ECM bioscaffold powder to three successive elastin extractions of one hour each, in 0.25M oxalic acid at 100° C. The amount of α-elastin determined in each extract was normalized to weight of wet tissue or weight of Adv ECM powder.

Formation of ECM Bioscaffold Hydrogels. Hydrogels were formulated from ECM bioscaffold digests according to an established method (Freytes D O, et al. Preparation and rheological characterization of a gel form of the porcine urinary bladder matrix. Biomaterials. 2008; 29:1630-7) and with all preparations performed on ice. Briefly, the digest was diluted to the desired final concentration and neutralized to a pH of 7.4±0.2 in a solution of 10×PBS and 0.1 N NaOH (sodium hydroxide, Thermo Fisher Scientific).

Hydrogel Gelation Kinetics. Turbidimetric hydrogel gelation kinetics were determined for porcine and human Adv ECM bioscaffold-derived hydrogels (4-16 mg/mL) as described previously (Freytes D O, et al. 2008; 29:1630-7). Optical density readings from 100 μL aliquots of neutralized ECM digest were obtained in triplicate every 2 minutes at 405 nm for up to 2 hr using a spectrophotometer (TECAN, Germany). Normalized absorbance (NA) was determined by the following equation:

$$NA = \frac{A - A_0}{A_{max} - A_0}$$

where 'A' represents the absorbance reading at a particular time point, '$A_0$' represents the initial absorbance and 'Amax' represents the maximum absorbance. Additional metrics of ECM gelation determined include: the time required for 50% gelation, defined as '$t_{1/2}$'; the lag phase '$t_{lag}$', determined via extrapolation of the linear portion of the normalized absorbance curve; and the gelation speed 'S', calculated as the maximum slope of the growth region for the normalized absorbance curve.

Morphological Ultrastructure Characterization of Hydrogels. hAdv, pAdv, and pSIS ECM bioscaffold hydrogels were prepared at 8 mg/mL on 12 mm round cover glass (Thermo Fisher Scientific) and fixed in 2.5% glutaraldehyde (Electron Microscopy Sciences, Hatfield, Pa.) for 1 hour. Fixed hydrogels were rinsed three times for 15 minutes in 1×PBS, treated in osmium tetroxide for 1 hour, and further rinsed three times for 15 minutes in 1×PBS before dehydration in graded ethanol series for 15 minutes each (30%, 50%, 70%, 90%, 100%). Dehydrated specimens were then critical point dried with supercritical $CO_2$ (Leica Biosystems, Buffalo Grove, Ill.), allowing 15 minutes for processed hydrogels to soak before each purge cycle. Following critical point drying, samples were sputter coated with gold/palladium (Cressington Scientific Instruments, Watford, England) at a thickness of 4.6 nm. The surface morphology of hAdv, pAdv and pSIS ECM hydrogels was then examined using a JSM 6335F scanning electron microscope (Jeol USA, Inc., Peabody, Mass.) at 5,000× and 10,000× total magnification and compared with intact specimens of decellularized native human adventitia.

Isolation and Culture of Primary Adventitia-Derived Human Endothelial Cells. Primary endothelial cells were isolated from the adventitia of a human specimen of thoracic aorta from a healthy donor. Upon specimen acquisition in the lab within 1-2 hr of harvest, the adventitia was immediately stripped away from the medial layer and rinsed twice in ice-cold 1×PBS with 1% (v/v) penicillin/streptomycin and 1% (v/v) Fungizone (Invitrogen). Tissue was then finely minced using safety scalpels and rinsed in 1×PBS. The tissue and PBS were placed in a 70 μm molecular sieve. The pass-through was collected and held at 37° C. while remaining tissue was digested in DMEM (Life Technologies) containing 0.4% (w/v) collagenase type IV (Worthington Biochemical Corporation, Lakewood, N.J.) and 350 KU/mL DNase I (Sigma) for 30 min at 37° C. with gentle agitation. The digestion medium and tissue was passed through a 70 μm sieve and tissue was returned to fresh digestion medium for another 30 min at 37° C. with gentle agitation. Following a final straining through a 70 μm sieve and wash with 1×PBS, all filtrates were pooled and centrifuged at 400 g for 10 min at 4° C. Cells were plated in 75 cm2 culture flasks in endothelial growth medium (EGM, Cell Applications, San Diego, Calif.). Gentamycin (250 μg/mL, Thermo Fisher Scientific) was added for 24-48 hr. Cells were maintained in a humidified incubation chamber at 37° C. and 5% $CO_2$ and expanded for 1-2 passages. Primary endothelial cells were isolated from parent culture using fluorescence activated cell sorting (FACS).

For FACS-based isolation of endothelial cells, expanded adventitial cells were pelleted (~1-4×106 cells), incubated in 1 μL neat mouse serum (Sigma) on ice, protected from light, and labeled with the following fluorochrome-conjugated monoclonal mouse anti-human antibodies (2 μL per antibody): CD31-PE-Cy7 (Biolegend, San Diego, Calif., #303117), CD45-APC-Cy7 (BD Biosciences, San Jose, Calif., #348805), and CD34-ECD (#BD2709U), and CD56-PE-Cy5 (IM2654, both from Beckman Coulter, Indianapolis, Ind.). DAPI (200 ng/mL) was added to unfixed and unpermeabilized cell suspensions just prior to sorting to discriminate live from dead/apoptotic cells. Cells were sorted using three of a five-laser MoFlo Astrios high speed cell sorter (Beckman Coulter, University of Pittsburgh Cancer Institute Flow Cytometry Core Facility) enclosed in a Class II biosafety cabinet. Cells were sorted as previously described (Zimmerlin L, et al. Stromal vascular progenitors in adult human adipose tissue. Cytometry A. 2010; 77:22-30) on the basis of a mature endothelial surface proteome of (CD56-/CD45-/CD34-/CD31+) into 6-well plates containing EGM with gentamicin, expanded for 1-2 passages with media replenishment every second day until cryopreservation.

Endothelial Cell Branching Assay. Cell culture substrates were prepared by coating the surface of wells in a 48-well culture plate with growth factor-reduced (GFR) Matrigel (Corning) prepared in the presence or absence of freshly-digested pAdv or pSIS ECM bioscaffold (250 μg/mL). Gelation was allowed to occur in a humidified 37° C. incubator for 1 hr. Primary human adventitia-derived endothelial cells were seeded in triplicate on gel-based substrates at a density of $1.5 \times 10^4$ cells/$cm^2$ in EGM. Digestion buffer (1 mg/ml pepsin in 0.1N HCl) and DMSO only controls were performed in adjacent wells. Where indicated, cells were treated with 100 nM PD173074. To assess endothelial cell branching formation of tube-like structures, large frame images were captured at 7 hr post-cell seeding using a Nikon Eclipse TE2000-E microscope equipped with an imaging array CoolSNAP ES2 monochrome camera and NIS Elements Software (Nikon Inc., Melville, N.Y.). Total number and length of tube-like structures were quantified using NIS Elements Software.

Chick Chorioallantoic Membrane (CAM) Model of In Vivo Angiogenesis. The CAM assay was modified from our established protocols (Smith J D, et al. The use of quantum dots for analysis of chick CAM vasculature. Microvasc Res. 2007; 73:75-83 and Smith J D, et al. Improved growth factor directed vascularization into fibrin constructs through inclusion of additional extracellular molecules. Microvasc Res. 2007; 73:84-94). White Leghorn eggs were purchased from a local farm and incubated at 37° C. and 70% humidity (G.Q.F. Manufacturing Co., Savannah, Ga.). On day 3 of incubation, eggs were cracked into sterile petri dishes and incubated for 10 days. Fibrin scaffolds to be placed on the chicken chorioallantoic membrane (CAM) were prepared similar to previously described methods (Smith J D, et al. Improved growth factor directed vascularization into fibrin constructs through inclusion of additional extracellular molecules. Microvasc Res. 2007; 73:84-94; Smith J D, et al. The use of quantum dots for analysis of chick CAM vasculature. Microvasc Res. 2007; 73:75-83; and Jadlowiec J, et al. Endocrinology. 2005; 146:3765-72). Briefly, final concentrations of 5 mg/mL bovine fibrinogen, 1 U/mL aprotinin (both from Enzyme Research Labs, South Bend, Ind.) were buffered in 1×PBS, pH 7.4. Addition of digestion buffer (1 mg/mL pepsin in 0.1N HCl) to fibrin scaffolds served as a negative control for angiogenic response. The final concentration of pAdv ECM bioscaffold in fibrin gels was varied from 50 μg/mL to 500 μg/mL in the presence or absence of the FGF2 inhibitor PD173074 (100 nM in DMSO) or vehicle control (0.05% (v/v) DMSO). Scaffold components were mixed and incubated at 37° C. for 30 min. Human thrombin (Enzyme Research laboratory, South Bend, Ind.) was added to 1 U/mL to initiate fibrin polymerization and incubated at 37° C. for 60 min in a 48-well plate (Corning, N.Y.). Fibrin scaffolds supplemented with the test materials were placed on the CAM and incubated at 37° C. with 70% humidity.

After 72 hr on the CAM, bright field images of the scaffolds and surrounding vasculature resulting from the angiogenic response were captured using a 3MP color camera mounted on a stereomicroscope (AmScope, Irvine, Calif.) at a 7.5× magnification. Endothelial cells of the chick vasculature were labelled by micro-injecting DyLight® 650-labeled tomato lectin (Vector labs, Burlingame, Calif.) and incubated for 15 min prior to excising the scaffold and the surrounding CAM. The harvested tissue was fixed in 10% neutral-buffered formalin (Sigma, St. Louis, Mo.) for 48 hr, washed in 1×PBS thrice and cryoprotected for 72 hr in 30% sucrose solution before processing for histological evaluation. The scaffolds were dissected in half, embedded in Tissue-Tek OCT (Sakura Finetek USA Inc., Torrance, Calif.) and 60 μm thick sections were cut using a Microm HM5000M cryostat microtome (Thermo Fisher Scientific). The sections were stained with Hoechst 33342 solution (Thermo Fisher Scientific) and imaged using Zeiss LSM 880 confocal microscope using a 10× objective. Tile scanning was performed and the images were stitched using ZEN black microscope and imaging software (Carl Zeiss Microscopy, Thornwood, N.Y.).

Protein Array. Decellularized human adventitia from normal (n=7 patients) and aneurysmal (n=28 patients) aortic specimens, and porcine adventitia and SIS were analyzed for the presence of angiogenesis-related proteins using the Protein Profiler™ Array Human Angiogenesis Kit (R&D Systems, Minneapolis, Minn.) according to the manufacturer's instructions. Briefly, lyophilized ECMs were resuspended in RIPA buffer containing protease inhibitors and homogenized using a douncer. Total protein concentration was assessed using a bicinchoninic acid assay (Thermo Scientific) and 300 μg of total protein was used as input for the array. Densitometry measurements were made from duplicate spots of each protein using ImageJ software (National Institutes of Health, USA).

Statistical Analysis. All experiments were repeated at least two times. Pairwise comparisons in quantitative measures were made between treatments and controls using an unpaired two-tailed Student's T test. Quantitative data provided in the results section represent the mean±standard deviation. A p value of less than 0.05 was considered statistically significant.

Results

Adv Bioscaffold Characterization. Adventitia stripped from porcine and human aortic media were decellularized, lyophilized, and ground into a fine powder (FIG. 9(A)). pH-neutralized pepsin-digested ECM bioscaffolds formed hydrogels at 37° C. (FIG. 9(B)). Qualitative assessment of DNA content using gel electrophoresis revealed lower DNA content in hAdv and pAdv bioscaffolds when compared with native specimens (FIG. 9(C)). Total DNA content was found to be <40 ng/mg tissue and <350 ng/mg dry tissue weight for hAdv and pAdv bioscaffolds, respectively and <80 ng/mg for pSIS bioscaffolds. These pAdv and hAdv bioscaffolds also retained appreciable collagen and α-elastin (Table 1).

TABLE 1

Pepsin-soluble collagen and α-elastin content in native adventitia and adventitia-derived ECM digest from porcine and human aorta. Data are shown as mean (standard deviation).

| Species | Specimen | Collagen (μg/mg tissue) | Elastin (μg/mg tissue) |
|---|---|---|---|
| Porcine | Native | 2.75 (0.54) | 3.61 (0.96) |
| | ECM Bioscaffold | 18.0 (3.10) | 1.95 (0.21) |
| Human | Native | 0.56 (0.08) | 1.35 (0.04) |
| | ECM Bioscaffold | 21.2 (0.56) | 3.71 (0.66) |

Adv Bioscaffold Hydrogels Exhibit Fiber-like Microarchitecture Similar to Native Adventitia. The matrix ultrastructure of decellularized human adventitia was investigated before the grinding and lyophilization steps of the ECM bioscaffold preparation (FIG. 10(A, B)). Observation of these specimens via scanning electron micrographs revealed an acellular fibrous microarchitecture (FIG. 10(A, B)). A similar microarchitecture was also observed in hydrogels produced from digested hAdv (FIG. 10(C, D)) and pAdv (FIG. 10(E, F)) bioscaffolds, which exhibited a thinner and straighter morphology. In comparison, hydrogels produced from digested pSIS bioscaffolds displayed thicker, more undulated fibers, with additional globular ECM apparently adhered to the fibers (FIG. 9G, H). The native-like fibrous matrix microarchitecture of adventitia was recapitulated following the decellularization, lyophilization, grinding, digesting, and gelation processes utilized to produce ECM bioscaffold hydrogels.

Gelation Kinetics for ECM Bioscaffold Hydrogels. Optical density of ECM hydrogels over time revealed a logarithmic curve during the gelation period at 37° C. As expected, increased optical density of the hydrogel was observed for higher concentrations of pAdv ECM bioscaffold (FIG. 11(A)). Ninety percent gelation occurred within 60 minutes and peak gelation was reached within 90 minutes (FIG. 11(A)). A plot of the normalized absorbance of pAdv, hAdv and pSIS ECM bioscaffolds during gelation revealed similar rates of gelation among all biomaterials tested (FIG. 11(B)). The speed (S), $t_{lag}$, and $t_{1/2}$ of gelation as calculated from optical density readings of ECM hydrogel formulations were similar at the 8 mg/mL concentration for pSIS and pAdv groups (Table 2).

TABLE 2

Turbidimetric analysis of porcine bioscaffold gelation kinetics. Representative calculations from one of three independent batches of pepsin-digested bioscaffolds are displayed. Data are shown as mean (standard deviation).

| Material | Density (mg/mL) | S (OD/min) | $t_{1/2}$ (min) | $t_{lag}$ (min) |
|---|---|---|---|---|
| SIS | 8 | 0.04 (0.002) | 29.3 (2.31) | 17.59 (2.17) |
| Adventitia | 4 | 0.02 (0.001) | 30.7 (1.15) | 1.96 (1.26) |
| | 8 | 0.03 (0.005) | 32.0 (3.46) | 9.76 (8.09) |
| | 16 | 0.03 (0.002) | 34.0 (2.00) | 14.16 (3.73) |

S, $t_{1/2}$, and tlag indicate gelation speed, time required for 50% gelation, and lag phase respectively.
O.D. = optical density.

Figure 12:
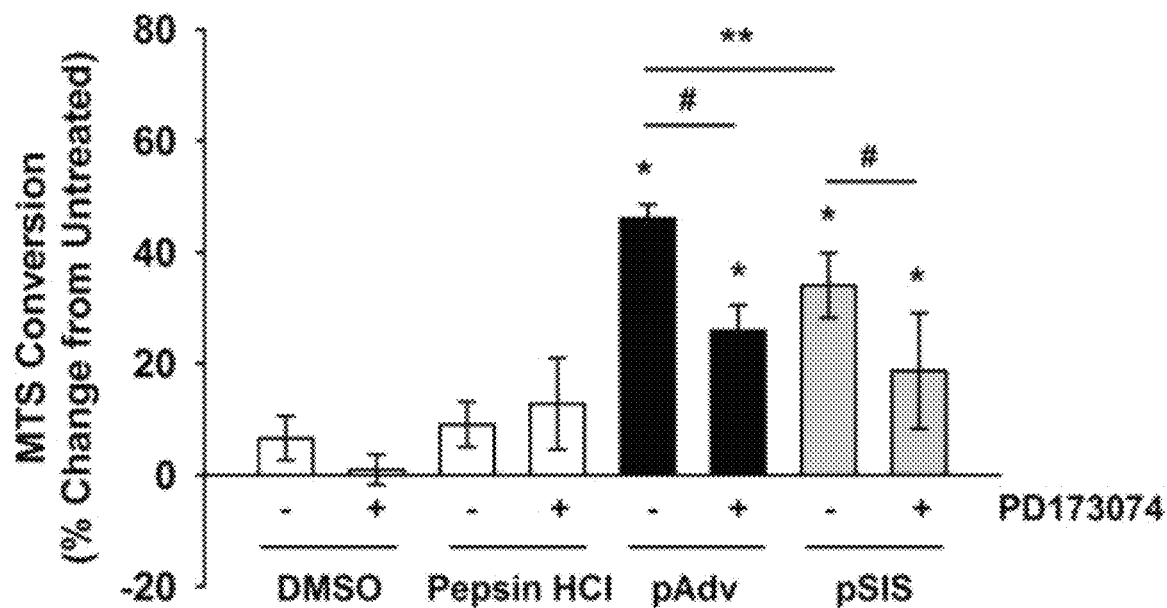
FIG. 12. FGF2-mediated stimulation of primary endothelial cell proliferation by ECMs. Primary human adventitia-derived endothelial cells were cultured in the presence of 10 µg/mL porcine adventitial (pAdv, solid bars) or porcine small intestinal submucosa (pSIS, gray bars) ECM. Cells in their basal culture medium, FGF2 inhibitor alone (100 nM PD173074 in DMSO), or an equivalent volume of DMSO and digestion buffer (1 mg/mL pepsin in 0.01 N HCl) served as controls (open bars). Quantification of MTS [3-(4,5-dimethylthiazol-2-yl)-5-(3-carboxymethoxyphenyl)-2-(4-sulfophenyl)-2H-tetrazolium] conversion was performed after 72 hr of exposure to the above conditions using a commercial assay and results were expressed as percent change of untreated cells. One representative of three independent experiments is displayed. Bars represent mean of four assay replicates ±standard deviation. * indicates p<0.05 when compared with untreated condition, **indicates p<0.02, and # indicates p<0.005.

Mitogenic Activity of Adv Bioscaffolds is FGF2-Mediated. Primary human endothelial cells isolated from the aortic adventitia exhibited increased cell proliferation with treatment of pAdv ECM bioscaffold when compared to cells in their basal growth medium (46.1±2.5 vs. 0.0±7.5%, p=0.0005) (FIG. 12). Treatment of endothelial cells with pSIS ECM bioscaffolds increased cell number when compared with control cells (34.0±5.8 vs. 0.0±7.5%, p=0.0005). pAdv ECM bioscaffold was found to be a more potent mitogen when compared with an equivalent dose of pSIS ECM bioscaffold (46.1±2.5 vs. 34.0±5.8%, p=0.018). Furthermore, the effect of both ECMs was in part mediated by FGF2 since inhibition of the FGF2 signaling pathway with PD173074 prevented increases in cell number by pAdv ECM bioscaffold (25.9±4.6 vs. 46.1±2.5%, p=0.001) and pSIS ECM bioscaffold (18.7±10.4 vs. 34.0±5.8%, p=0.05). Elevated cell proliferation persisted even in the presence of FGF2 inhibitor for both pAdv ECM bioscaffold (25.9±4.6 vs. 0.0±7.5%, p=0.002) and pSIS ECM bioscaffold (18.7±10.4 vs. 0.0±7.5%, p=0.03).

Figure 13A:
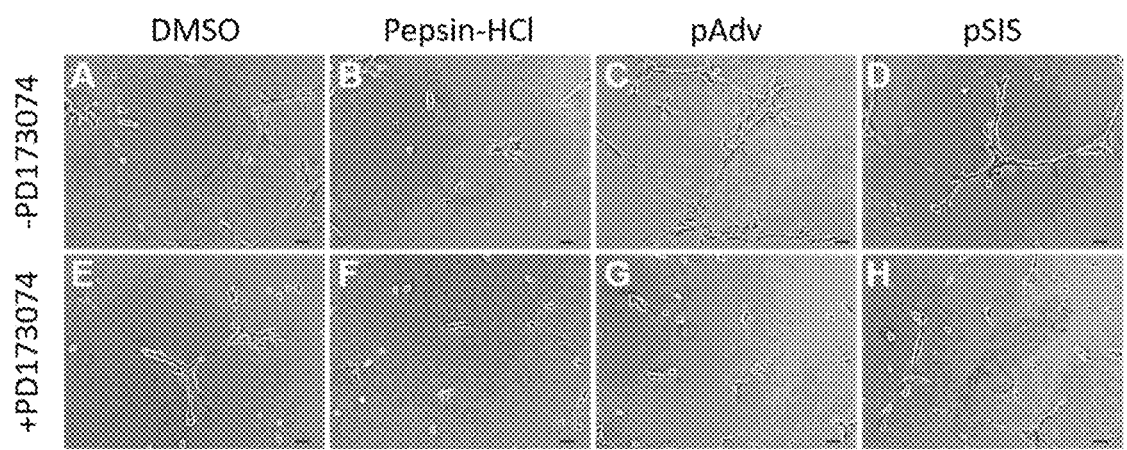
FIGS. 13A-13C. Effect of ECM bioscaffolds on network formation of tube-like structures in vitro.
Figure 13B:
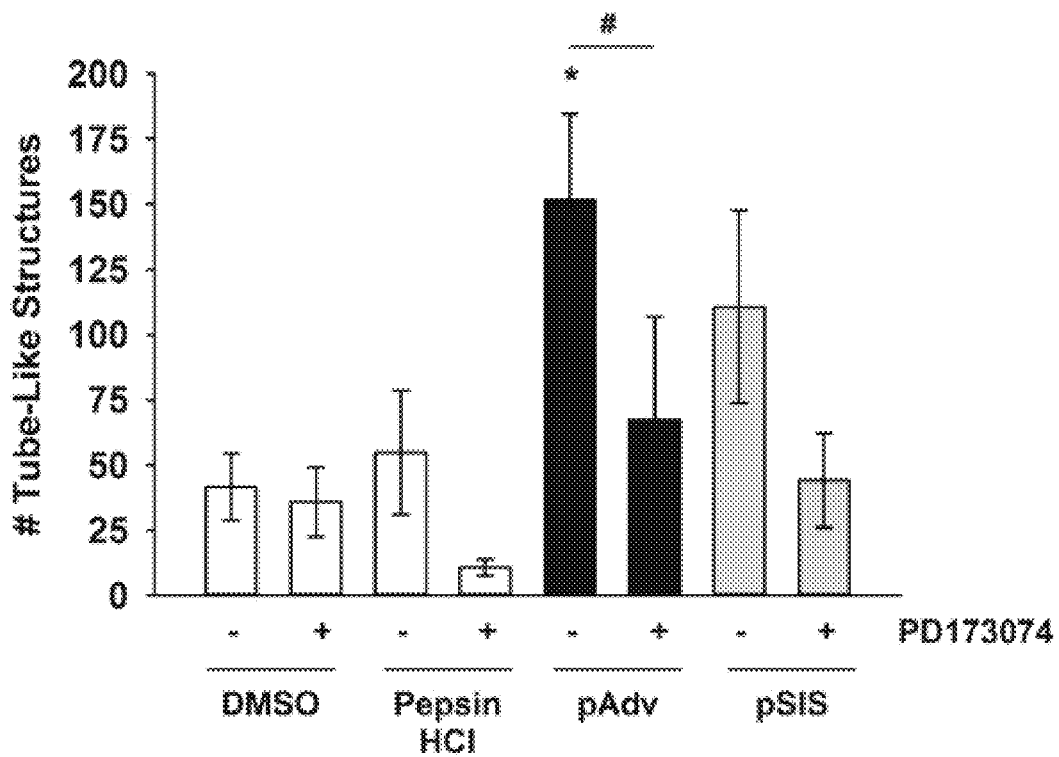
Figure 13C:
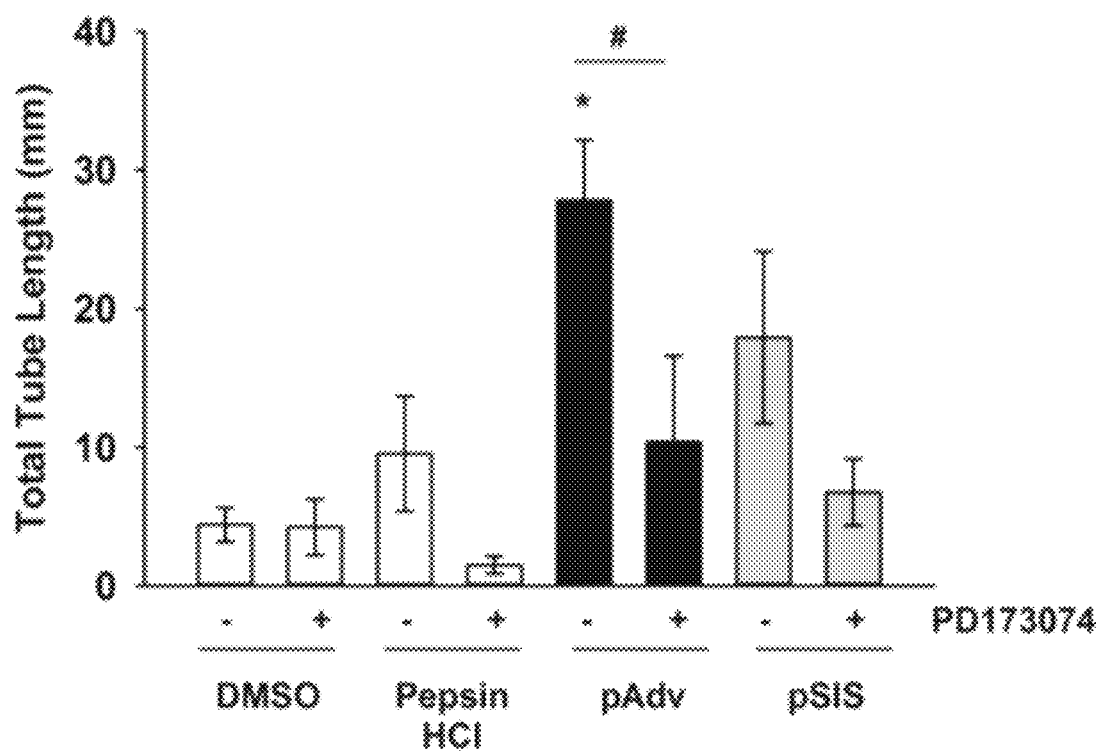

Adv Bioscaffolds Promote Tube-like Structures In Vitro via FGF2. There was minimal formation of tube-like structures by human adventitia-derived endothelial cells on GFR-Matrigel substrates alone (FIG. 13(A)) or substrates supplemented with pepsin HCl (FIG. 13(B)). Addition of pAdv ECM (FIG. 13(C)) and pSIS ECM (FIG. 13(D)) bioscaffolds to GFR-Matrigel substrates enhanced formation of tube-like structures by endothelial cells when compared with cells cultured on Matrigel alone (FIG. 13(A)) and substrates supplemented with pepsin HCl digestion buffer alone (FIG. 13(B)). Addition of the FGF2 inhibitor PD173074 did not affect tube-like formation on Matrigel alone (FIG. 13(E)) or pepsin HCl-supplemented substrates (FIG. 13(F)). Conversely, PD173074 decreased the tube-like formation on pAdv ECM bioscaffold (FIG. 13(G)) and pSIS ECM bioscaffold-supplemented substrates (FIG. 13(H)) when compared with cells cultured on ECM bioscaffold-supplemented substrates in the absence of FGF2 inhibitor (FIG. 13(C, D), respectively).

Quantification of the number (FIG. 13B) and total length (FIG. 13C) of tube-like structures was consistent with our qualitative observations and all values for treated cells were compared with pepsin-HCl controls. We noted minimal endothelial cell branching on Matrigel alone in the presence of DMSO or PD173074 added to the culture medium. We observed an increase in both the number and total length of tube-like structures on pAdv ECM bioscaffold containing substrates when compared with pepsin-HCl controls (151.7±33.01 vs 54.7±23.80 tubes, respectively, p=0.017 and 27.8±4.34 vs 9.5±4.15 mm, respectively, p=0.006). The presence of FGF2 inhibitor decreased the number and length of tube-like structures when compared with the absence of inhibitor for pAdv ECM bioscaffold (67.0±39.89 vs 151.7±33.01 tubes, p=0.049 and 10.4±6.20 vs 27.8±4.34 mm, p=0.020). A similar trend was noted for cells cultured on pSIS ECM-supplemented substrates when compared with pepsin-HCl controls, an observation which did not reach statistical significance (110.7±36.95 vs 54.7±23.80 tubes, respectively, p=0.104 and 17.9±6.23 vs 9.5±4.15 mm, respectively, p=0.135). The effect of FGF2 inhibition on tube-like formation on pSIS ECM-supplemented substrates was similar to that of pAdv ECM for both tube number and total tube length when compared with pepsin-HCl control but did not reach 95% confidence (44.0±18.08 vs 110.7±36.95 tubes, respectively, p=0.069 and 6.7±2.42 vs 17.9±6.23 mm, respectively, p=0.075).

Figure 14A:
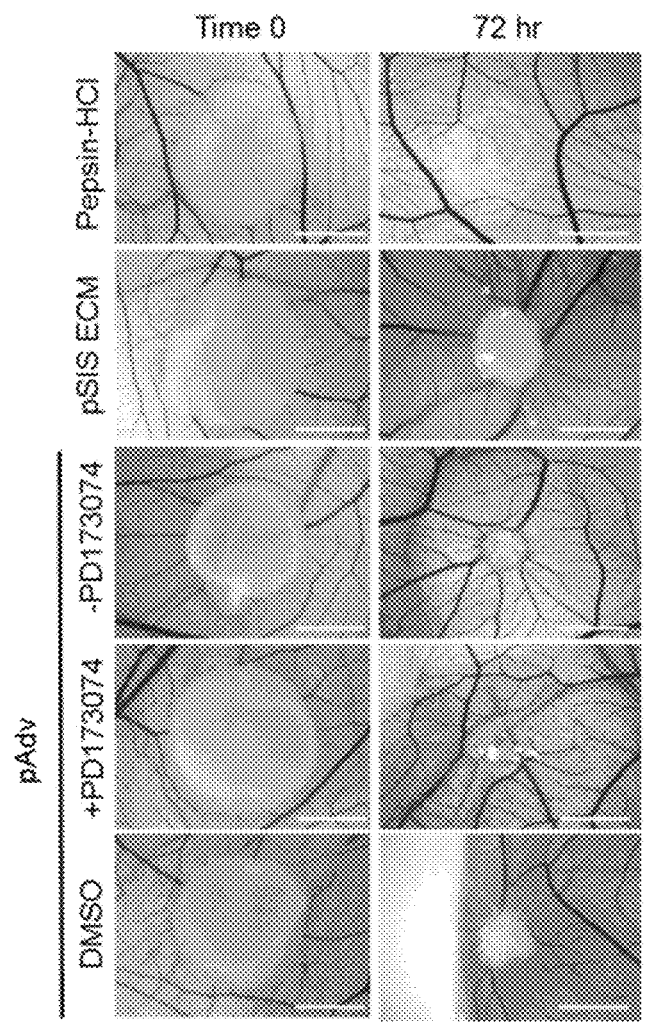
FIGS. 14A-14D. Effect of ECM bioscaffolds on angiogenesis in vivo.
Figure 14B:
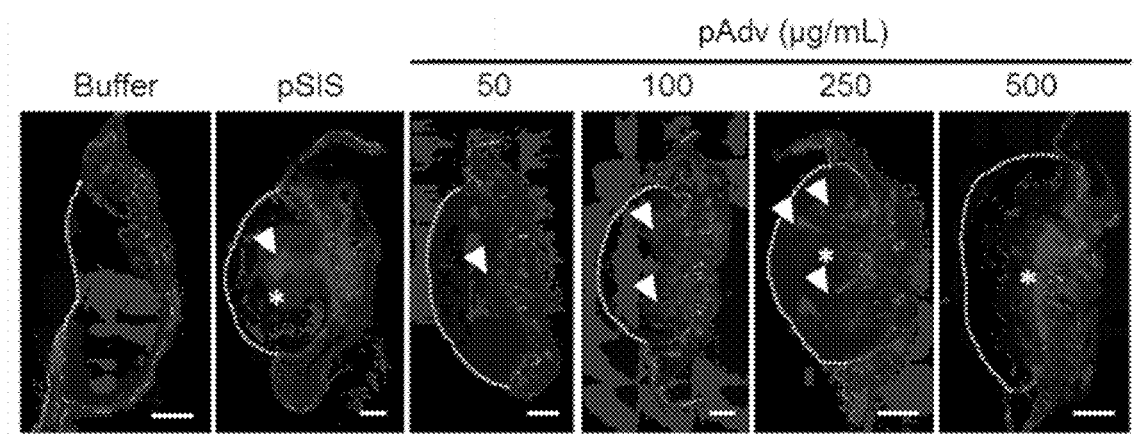
Figure 14C:
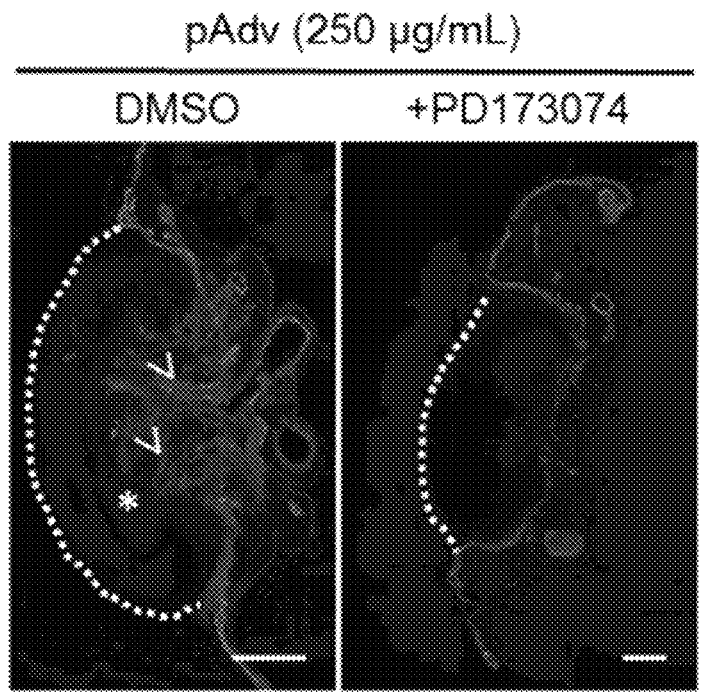
Figure 14D:
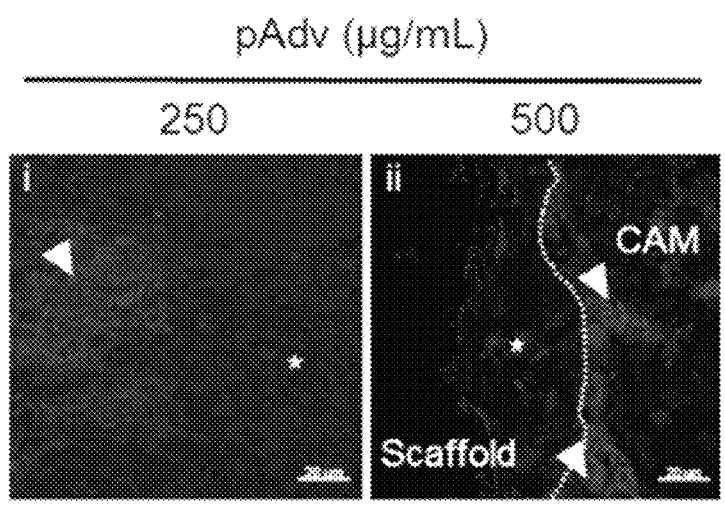

In Vivo Angiogenic Activity of pAdv Bioscaffolds. To evaluate the in vivo angiogenic potential of pAdv ECM bioscaffold, we employed the chick CAM model for angiogenesis. Qualitative inspection of pSIS ECM bioscaffold and pAdv ECM bioscaffold-loaded fibrin scaffolds after 72 hr revealed approximately the same level of angiogenic activity evidenced by the "spoke-wheel" pattern of chick vasculature around the perimeter of the scaffolds (FIG. 14A). Digestion buffer-loaded scaffolds did not elicit any angiogenic response after 72 hr. Vascular invasion into the scaffold occurred in a dose dependent manner with increasing pAdv ECM bioscaffold concentrations up to 250 µg/mL (FIG. 14B, arrowheads). Although 50-500 µg/mL pAdv ECM bioscaffold all resulted in a spoke-wheel pattern around the scaffold (FIG. 14A and FIG. 17), histological examination revealed abrogated a vascular invasion front at the highest dose of pAdv ECM (500 µg/mL) (FIG. 14B). Addition of the FGF2 inhibitor PD173074 completely inhibited pAdv ECM bioscaffold (250 µg/mL)-induced angiogenesis and inclusion of the drug vehicle DMSO alone had no effect on pro-angiogenic effects of pAdv ECM bioscaffold (FIG. 14C). We noted chemoattraction of lectin-negative cells invading pSIS and pAdv ECM-loaded scaffolds (FIG. 14B, asterix) ahead of a vascular front of migrating lectin-positive cells (FIG. 14B, arrowheads). Representative higher magnification images of this phenomenon for pAdv ECM-loaded scaffolds are displayed in FIG. 14D. We observed an avascular zone of lectin-negative cells within the pAdv ECM-loaded (250 µg/mL) scaffold (FIG. 14D(i), asterix), preceding invasion of migrating lectin-positive cells into the scaffold (FIG. 14D(i), arrowhead). At higher concentrations of pAdv ECM (500 µg/mL), lectin-negative cells invaded the scaffold whereas lectin-positive cells abutted and did not traverse the scaffold/CAM interface (FIG. 14D(ii)).

Detection of Angiogenesis-Related Proteins in ECM Bioscaffolds. We detected the presence of all 55 proteins on an angiogenesis-related commercial protein array in specimens of pAdv and pSIS ECM bioscaffolds as well as hAdv bioscaffolds isolated from normal and aneurysmal patients (FIG. 15). A complete list of all array proteins which were detected and densitometry values are displayed in FIG. 16. Qualitative inspection of array blots revealed that FGF2 was detected in all ECM bioscaffolds (FIG. 15, B19, B20). FGF1 and FGF2 (FIG. 15, B17, B18, B19, B20, respectively) were more abundant in pSIS ECM bioscaffold when compared with pAdv ECM bioscaffold (122.0±4.43 vs 43.3±0.7 pixel density (arbitrary units, p=0.022 and 100.2±0.56 vs 43.5±0.46 pixel density, respectively). Eight other angiogenesis-related factors were more abundant in pSIS ECM than in pAdv ECM bioscaffolds (FIG. 16). Interestingly, 19 proteins, including FGF2, were found to be in lower levels in hAdv ECM bioscaffold prepared from aneurysmal human aorta (>42 mm in maximal orthogonal diameter) when compared with specimens of non-aneurysmal aorta (<34 mm) (FIG. 16). Of note, thrombospondin 1 (TSP1) was approximately 3 times more abundant than the average amount of all other proteins (60.0±1.91 vs. 19.9±1.34). None of the detected angiogenesis-related factors were found to be elevated in aneurysmal specimens when compared with normal specimens.

In this study, we prepared a new ECM bioscaffold-based hydrogel biomaterial from a perivascular microenvironment using decellularized human and porcine aortic adventitial specimens. We characterized these ECM bioscaffolds for their matrix protein composition, microarchitecture and signaling activities on primary human endothelial cells in vitro and in an in vivo model of angiogenesis.

We demonstrated that ECM hydrogels self-assembled from pepsin-digested decellularized adventitial tissue under physiological conditions of pH, ionic strength and temperature to resemble native adventitial ECM architecture. Hydrogels derived from hAdv and pAdv ECM bioscaffolds recapitulated fibrous matrix microarchitecture in striking similarity to that of native human adventitia. These Adv ECM hydrogels exhibited a fiber morphology that appeared to be straighter and less undulated than fibers of hydrogels derived from pSIS ECM bioscaffold. The noted differences in matrix fiber ultrastructure of these hydrogels are likely dependent on the tissue-specific protein milieu which is concordantly dictated by the unique biomechanical demands of that tissue. For example, the aorta is a resilient, highly elastic tissue that endures continuous cyclic loading without overt dilatation or rupture in the absence of aneurysmal disease. Contrarily, the intestine is more porous to facilitate nutrient absorption, which may explain the observed decreased fiber density and undulated fiber morphology following ECM bioscaffold gelation. While further testing will ultimately determine the biomechanical properties of adventitia-derived ECM hydrogels, the collagen- and elastin-containing ECM bioscaffold hydrogels exhibited microarchitectural mimicry of the native adventitia following gelation. Analysis of the gelation kinetics of Adv ECM bioscaffold hydrogels revealed a gelation rate profile similar to that of other tissue sources such as pSIS for similar concentrations. The observed similarity in gelation kinetics among pSIS and Adv ECM bioscaffold hydrogels was unexpected due to the assumed compositional differences in proteins of SIS and adventitial microenvironments. Since hydrogel formation involves interplay among self-assembling matrix proteins such as collagens and the process can be modulated by laminin, fibronectin, and proteoglycans, the interpretation of gelation activities is complex. The observed similarities between the pSIS and Adv ECM gelation kinetics suggest that unique tissues, even when processed by different decellularization procedures can be ultimately reconciled through the process of ECM bioscaffold gelation, which similarly converts these unique ECMs to a hydrogel form. ECM hydrogels across unique tissue sources could potentially be further tailored by modulating the concentration of ECM bioscaffold. We are interested in understanding the specific protein components and functionality of pAdv ECM hydrogels and the present work further focused on the inherent bioactive properties of porcine ECMs and their influence on the in vitro behavior of human adventitia-derived endothelial cells and on in vivo angiogenesis.

We evaluated the influence of endogenous FGF2 within pepsin-digested porcine ECM bioscaffolds on activities key to angiogenesis. pAdv and pSIS ECM bioscaffold-induced proliferation of endothelial cells was FGF2 mediated. The mitogenic activity of both the Adv and pSIS ECM bioscaffolds in the presence of FGF2 inhibitor remained elevated above untreated controls to indicate FGF2-independent signaling by ECM bioscaffolds that directs cell proliferation, consistent with findings in porcine urinary bladder and dermis ECMs. FGF2 also mediated the ECM-induced network formation of tube-like structures by human adventitia-derived endothelial cells.

pAdv ECM bioscaffolds exhibited greater mitogenic potency than pSIS ECM bioscaffold, despite the increased abundance of FGF1 and 2 in pSIS ECM bioscaffold relative to Adv ECM bioscaffold. Two interpretations can be made from this observation. First, the tissue-specific milieu of the adventitia is advantageous for endothelial cells derived from this locale perhaps through retention of other tissue-specific growth factor dependent and independent mitogenic signals. In addition or alternatively to this explanation, it is reasoned that bioactivity capabilities differ between pSIS and pAdv ECM bioscaffold preparations. Furthermore, we detected every protein probed by the array in all ECMs prepared in this study and the human-specific nature of the array precludes us from making direct comparisons of protein abundance in human versus porcine ECMs. Importantly, the presence of growth factors in ECM scaffolds, such as bioactive FGF2 might also contribute to maintenance of resident progenitor cell niches in the adventitia. The decreased abundance of several angiogenesis-related factors in human aneurysm raises numerous questions related to disease mechanisms and offers opportunities to engineer in vitro models of human disease using perivascular ECM bioscaffolds and evaluate the therapeutic potential of the xenogeneic ECM counterparts in vivo.

Using the chick CAM in vivo angiogenesis model, we demonstrated the in vivo angiogenic potential of pAdv ECM. The vascular invasion noted with increasing concentrations of pAdv ECM bioscaffold could be attributed to the higher concentration of FGF2 and other angiogenic factors in the scaffolds. We speculate that the invasion of migrating lectin-negative cells are macrophages preceding lectin-positive endothelial cells during angiogenesis in response to pAdv and pSIS ECM-loaded scaffolds. We explain the interesting observation of inhibited vessel invasion at the highest dose of 500 µg/mL pAdv ECM bioscaffold in one of two ways. Either the present anti-angiogenic factors such as TSP1 interfere with pro-angiogenic signals or negative feedback mechanisms in the CAM are engaged by high concentrations of pro-angiogenic factors. The complete abrogation of pAdv ECM bioscaffold in vivo angiogenic potential in the presence of FGF2 inhibitor strongly suggests that FGF2 is a major proangiogenic signal and potent regenerative factor in adventitial ECM. Although alternative matrix signaling such as mechano-transduction and integrin-mediated signaling contribute to increased cellular proliferation, a review of in vitro angiogenic and vasculogenic models by Morin and Tranquillo affirms that the majority of the reports stated a required addition of exogenous growth factors in order to achieve angiogenesis and/or vasculogenesis with combinations of endothelial cells and pericytes when ECM bioscaffolds were not utilized (Morin K T, Tranquillo R T. In vitro models of angiogenesis and vasculogenesis in fibrin gel. Experimental Cell Research. 2013; 319:2409-17). Recently, the in vivo angiogenic potential of pSIS bioscaffold hydrogels was associated with matrix degradation-dependent release of FGF2 and VEGF (Wang W, et al. Preparation and characterization of pro-angiogenic gel derived from small intestinal submucosa. *Acta Biomaterialia*. 2016; 29:135-48). Likewise, Adv ECM bioscaffold-derived hydrogels serve as a depot for signals such as FGF2 that influence cell behaviors important for blood vessel formation.

For clinical applications, a select few ECM bioscaffold-derived hydrogels would ideally be developed to invoke regeneration in most diseased organs. Additionally, tissue-specific ECM hydrogels can serve as natural biologic scaffolds which could be useful for discovery biology of disease mechanisms. Although ECM hydrogels from a variety of tissue sources exhibited inherent bioactivity, investigation of their impact on angiogenesis emerged only recently. These studies provided evidence that ECM bioscaffolds influence and interact with blood vessel cells. The angiogenic potential of hybrid scaffolds has been better studied using synthetic materials conjugated with unique combinations of tissue-derived angiogenic growth factors and must be precisely engineered for specific applications with engineered growth factor content and release profiles. ECM bioscaffolds offer a distinct advantage over synthetic constructs in their tissue-specific mimicry through multi-factorial structural and signaling capacities. Furthermore, hydrogels derived from ECM bioscaffolds can be tailored for specific tissue regeneration applications through choice of source tissue, density and method of delivery. Our findings collectively demonstrate that Adv ECM bioscaffold hydrogels are versatile biological scaffolds that are capable of both microstructural and growth factor-dependent signaling mimicry of the native adventitia microenvironment which together are important for desirable effects on cellular function of blood vessel lineages.

CONCLUSIONS

We reveal that perivascular tissue from the human and porcine aortic adventitia can be decellularized to derive ECM bioscaffolds and formulated into hydrogels that recapitulate native matrix fiber microarchitecture. pAdv ECM bioscaffolds retained bioactive signals that invoked FGF2-mediated human endothelial cell proliferation, network formation of tube-like structures in vitro, and angiogenesis in vivo. Several angiogenesis-related proteins, including FGF2, are present within Adv ECM bioscaffolds and many were less abundant in matrix prepared from specimens of human aneurysm. These findings provide support for the use of Adv ECM bioscaffolds in further study of vasculogenesis and angiogenesis in normal physiology in the setting of cardiovascular disease, and also provide novel therapeutic opportunities.

Example 7—In Vivo Assessment of Decellularized Porcine Aortic Adventitia ECM

Methods: The in vivo pro-angiogenic properties of porcine aortic adventitia ECM were assessed in a pilot assay using an adaptation of a previously established subcutaneous matrigel-plug mouse model (Passaniti, A., et al. (1992). A simple, quantitative method for assessing angiogenesis and antiangiogenic agents using reconstituted basement membrane, heparin, and fibroblast growth factor. *Laboratory investigation; a journal of technical methods and pathology*, 67(4), 519-528). Briefly, 6-8 week old C57BL6J mice (25-30 g) were anesthetized and four horizontal incisions (12 mm) were made on the dorsal side to create subcutaneous pocket for scaffold implantation. The scaffolds were prepared by casting 250 µL of 10 mg/mL fibrin (with or without neutralized porcine adventitia ECM bioscaffolds) in a standard 48 well plate. At 7 and 14 days post-implantation, Dylight® 650-tomato lectin was injected via the tail vein to label the vasculature. Fifteen minutes post injection, animals were sacrificed and the scaffold along with the surrounding tissue was harvested and fixed in 10% neutral buffered formalin for 48 hours. Half of each specimen was allocated for analysis of hematoxylin and eosin (H&E) and Masson's Trichrome stained paraffin embedded section. The other half of each specimen were evaluated for lectin-labeled vasculature in cryosections.

Figure 18:
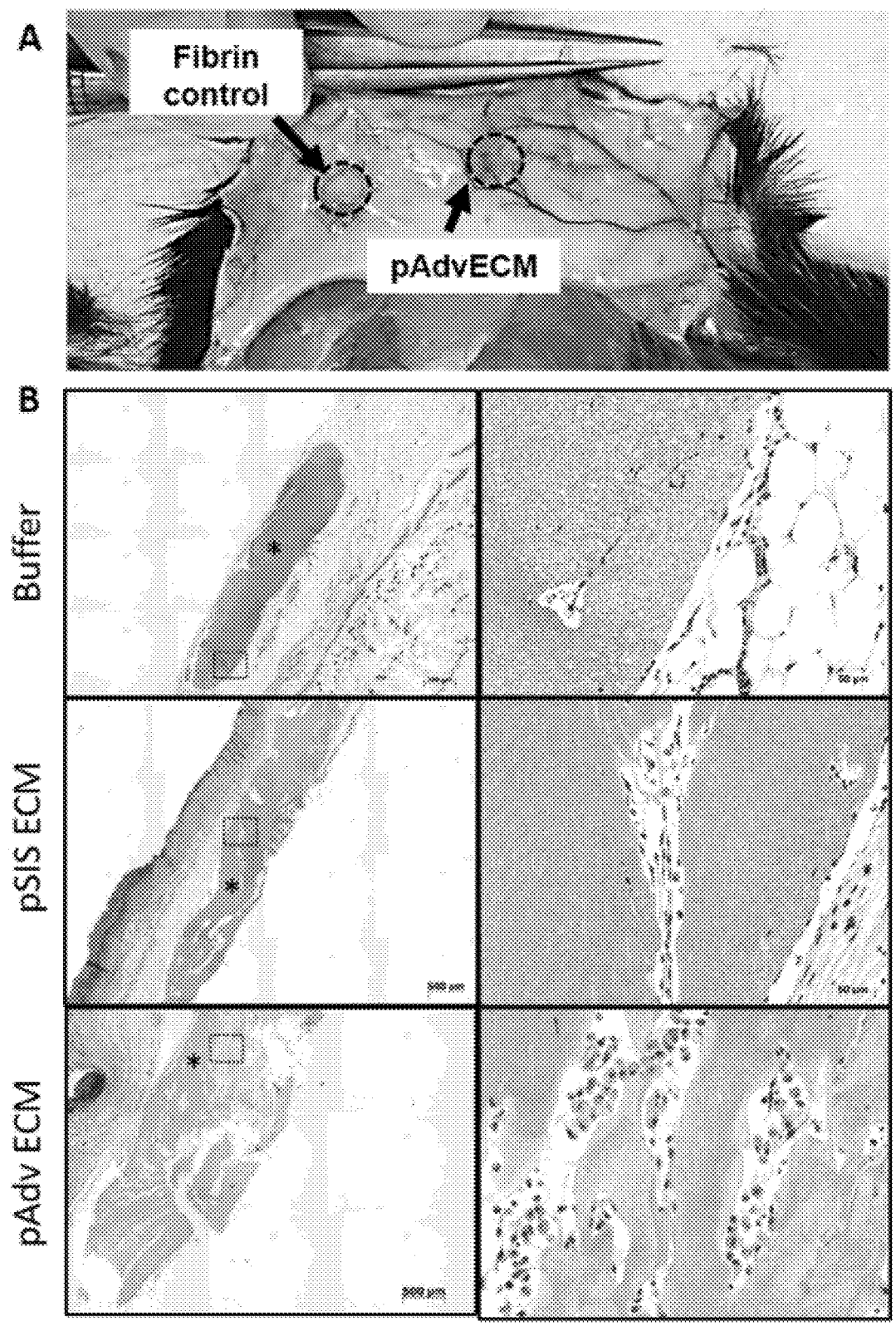
FIG. 18. Photograph (A) and photomicrographs (B) showing the results described in Example 7. (A) shows that pAdv ECM-loaded fibrin plug invoked an angiogenic response. (B) shows Representative H&E-stained paraffin-embedded sections reveal more cell infiltration within pSIS and pAdv ECM-loaded fibrin scaffolds (denoted by an asterix) when compared with buffer loaded scaffolds, as described in Example 7. For (B), scale bars=500 μm for left side panels and 50 μm for right side panels.

Results: Preliminary results revealed increased pro-angiogenic activity of pAdv ECM-loaded fibrin scaffolds when compared with unloaded fibrin scaffolds (FIG. 18 (A)), consistent with our observations of angiogenesis with pSIS and pAdv ECM scaffolds in the CAM model described above. Qualitative microscopic inspection of H&E-stained paraffin embedded sections revealed greater cell infiltration (speculatively macrophages) of the scaffolds 14 days after implantation with pSIS and pAdv ECM-loaded fibrin when compared with unloaded fibrin alone or gels supplemented with digestion buffer alone (FIG. 18(B)). Furthermore, the pAdv ECM-loaded scaffold seemed to be more degraded with more infiltrating cells than scaffolds loaded with SIS ECM.

The following clauses provide examples of various aspects of the invention described herein.

1. A method of preparing an extracellular matrix (ECM) material, comprising:
   a. incubating vascular adventitial tissue in a zwitterionic detergent, wherein the vascular adventitial tissue is optionally bovine, ovine, or porcine;
   b. incubating the tissue in Trypsin-EDTA;
   c. incubating the tissue with an anionic detergent;
   d. disinfecting the tissue, optionally with peracetic acid, producing a decellularized ECM material;
   e. lyophilizing the decellularized ECM material;
   f. comminuting the decellularized ECM material;
   g. partially or completely solubilizing the decellularized ECM material with an acid protease to produce solubilized ECM; and
   h. neutralizing the solubilized ECM to produce an ECM pre-gel.
2. The method of clause 1, wherein the adventitial tissue is aortic adventitia.
3. The method of any one of clauses 1 or 2, further comprising gelling the ECM pre-gel at a temperature at which the ECM pre-gel gels to produce an ECM gel.
4. The method of any one of clauses 1-3, wherein the decellularized ECM material is not completely digested with the acid protease, producing an ECM pre-gel that is able to gel at 37° C. comprising undigested decellularized ECM particles.
5. The method of any one of clauses 1-4, further comprising including one or more washing steps from prior to step e.
6. The method of clause 5, wherein the one or more washing steps comprises washing the tissue or material with phosphate-buffered saline, saline, and/or water.
7. The method of any one of clauses 1-6, wherein the ECM material is prepared without a dialysis step or a cross-linking step.
8. The method of any one of clauses 1-7, wherein the zwitterionic detergent is CHAPS.
9. The method of any one of clauses 1-8, wherein the anionic detergent is SDS.
10. The method of any one of clauses 1-9, wherein the acid protease is pepsin.
11. The method of any one of clauses 1-10, wherein the decellularized ECM material is solubilized with an acid protease in a solution having a pH of from 1 to 4, from 1 to 2, or 2.0±0.3.
12. The method of any one of clauses 1-11, comprising dispersing the ECM material in a natural or a synthetic polymer composition.
13. The method of clause 12, wherein the natural or a synthetic polymer composition is one or more of: a second ECM material, fibrin, collagen, polyester (PE), polyurethane (PU), poly(ester urethane) urea (PEUU), poly(ether ester urethane) urea (PEEUU), poly(ester carbonate urethane)urea PECUU), poly(carbonate urethane) urea (PCUU) copolymer, polyolefin (polyalkene), polycarbonate, polyanhydride, polyether, polyurea, polyurethane, polyketone, and fluoropolymer.
14. The method of clause 12 or 13, wherein the ECM material is mixed with the natural or synthetic polymer composition prior to or during gelation of the ECM material.
15. The method of clause 12, wherein the pre-gel is mixed with fibrin and fibrinogen and is gelled while the fibrin is cross-linked with the fibrinogen.
16. An ECM composition comprising devitalized, acid-protease-digested aortic adventitial tissue, having a pH of from 6.8 to 7.8.
17. The ECM composition of clause 16, wherein the composition is a gel and as compared to acid-protease-digested porcine small intestine submucosa, the gel comprises longer fibers and at least 50% lower FGF-1 and/or FGF-2 content, and optionally has increased HB-EGF (Heparin Binding EGF Like Growth Factor) content and/or lower content of one or more of Angiopoietin 2; Endostatin; IGFBP1 (Insulin Like Growth Factor Binding Protein 1); PTX3 (Pentraxin 3); Prolactin; Serpin B5; and/or TIMP4 (TIMP Metallopeptidase Inhibitor 4), and optionally has at least 50% lower FGF-1 and/or FGF-2 content, increased HB-EGF (Heparin Binding EGF Like Growth Factor) content, and lower content of Angiopoietin 2; Endostatin; IGFBP1 (Insulin Like Growth Factor Binding Protein 1); PTX3 (Pentraxin 3); Prolactin; Serpin B5; and TIMP4 (TIMP Metallopeptidase Inhibitor 4).
18. The composition of clause 16 or 17, wherein the devitalized, acid-protease-digested aortic adventitial tissue is not dialyzed or chemically crosslinked.
19. A method of treating an aneurysm in a patient, comprising administering to a surface of a blood vessel having an aneurysm, a devitalized, acid-protease-digested vascular adventitial tissue, having a pH of from 6.8 to 7.8, wherein the vascular adventitial tissue is optionally aortic adventitial tissue.
20. The method of clause 19, wherein the blood vessel is the aorta of the patient.
21. The method of clause 19 or 20, wherein the devitalized, acid-protease-digested vascular adventitial tissue is prepared by:
   a. incubating vascular adventitial tissue, such as aortic adventitial tissue, in a zwitterionic detergent, wherein the vascular adventitial tissue is optionally bovine, ovine, or porcine;
   b. incubating the tissue in Trypsin-EDTA;
   c. incubating the tissue with an anionic detergent;
   d. disinfecting the tissue, optionally with peracetic acid, producing a decellularized ECM material;
   e. lyophilizing the decellularized ECM material;
   f. comminuting the decellularized ECM material;
   g. partially or completely solubilizing the decellularized ECM material with an acid protease to produce solubilized ECM;
   h. neutralizing the solubilized ECM to produce an ECM pre-gel, and
   i. optionally, gelling the ECM pre-gel at a temperature at which the ECM pre-gel gels to produce an ECM gel.
22. A method of vascularizing or re-vascularizing living tissue in a patient, comprising administering to a surface of a tissue ex vivo, or in vivo, a devitalized, acid-protease-digested vascular adventitial tissue, having a pH of from 6.8 to 7.8, wherein the vascular adventitial tissue is optionally aortic adventitial tissue.
23. The method of clause 19, wherein the tissue is a living blood vessel.
24. The method of clause 19, wherein the tissue is a wound of a patient, optionally a skin wound, a diabetic ulcer, or a diabetic foot ulcer, and the devitalized, acid-protease-digested vascular adventitial tissue is administered to the wound.

25. The method of clause 19, wherein the tissue is living bone tissue of a patient, optionally a damaged bone, or bone exhibiting osteoporosis, and the devitalized, acid-protease-digested vascular adventitial tissue is administered to the bone.

26. The method of clause 19, wherein the tissue is myocardium and/or vasculature thereof in a patient, optionally a wound in a patient's myocardium or an infarct, and the devitalized, acid-protease-digested vascular adventitial tissue is administered to the patient's myocardium, and optionally to the wound or infarct in the patient's myocardium.

27. The method of any one of clauses 22-26, wherein the devitalized, acid-protease-digested vascular adventitial tissue is prepared by:
   a. incubating vascular adventitial tissue, such as aortic adventitial tissue, in a zwitterionic detergent, wherein the vascular adventitial tissue is optionally bovine, ovine, or porcine;
   b. incubating the tissue in Trypsin-EDTA;
   c. incubating the tissue with an anionic detergent;
   d. disinfecting the tissue, optionally with peracetic acid, producing a decellularized ECM material;
   e. lyophilizing the decellularized ECM material;
   f. comminuting the decellularized ECM material;
   g. partially or completely solubilizing the decellularized ECM material with an acid protease to produce solubilized ECM;
   h. neutralizing the solubilized ECM to produce an ECM pre-gel, and
   i. optionally, gelling the ECM pre-gel at a temperature at which the ECM pre-gel gels to produce an ECM gel.

Having described this invention, it will be understood to those of ordinary skill in the art that the same can be performed within a wide and equivalent range of conditions, formulations and other parameters without affecting the scope of the invention or any embodiment thereof.

We claim:

1. A method of vascularizing or re-vascularizing living tissue in a patient, comprising administering to a surface of a vascular graft, in vivo, an extracellular matrix (ECM) composition comprising devitalized, acid-protease-digested ECM derived from vascular adventitial tissue delaminated from the medial layer and having a pH of from 6.8 to 7.8, wherein the ECM composition does not include ECM derived from the medial layer.

2. The method of claim 1, wherein the vascular adventitial tissue is aortic adventitial tissue.

3. The method of claim 1, wherein the vascular adventitial tissue is arterial adventitial tissue.

4. The method of claim 1, wherein the vascular adventitial tissue is bovine, ovine, or porcine.

5. The method of claim 1, wherein the devitalized, acid-protease-digested ECM is not dialyzed or chemically cross-linked.

6. The method of claim 1, wherein the composition forms a gel when warmed to 37° C.

7. The method of claim 1, wherein the vascular graft comprises living tissue.

8. The method of claim 7, wherein the living tissue is vascular tissue.

9. The method of claim 1, wherein the graft comprises an inorganic material.

10. The method of claim 1, wherein the living tissue is myocardium in a patient, and the ECM composition is administered to the patient's myocardium.

11. The method of claim 1, wherein the ECM composition is coated onto a surface of the vascular graft.

12. The method of claim 1, wherein the ECM composition is seeded with one or more cells.

13. The method of claim 12, wherein the one or more cells comprise one or more stem cells.

14. The method of claim 1, wherein the ECM composition comprises one or more therapeutic agents.

15. A method of vascularizing or re-vascularizing living tissue in a patient, comprising:
   coating a surface of a vascular graft, ex vivo, with an extracellular matrix (ECM) composition comprising devitalized, acid-protease-digested ECM derived from vascular adventitial tissue delaminated from the medial layer and having a pH of from 6.8 to 7.8, wherein the ECM composition does not include ECM derived from the medial layer, and
   implanting the coated vascular graft in the patient's vasculature.

16. The method of claim 15, wherein the vascular adventitial tissue is aortic adventitial tissue or arterial adventitial tissue.

17. The method of claim 15, wherein the ECM composition is seeded with one or more stem cells.

18. The method of claim 15, wherein the vascular graft comprises living tissue.

19. The method of claim 18, wherein the living tissue is vascular tissue.

20. The method of claim 15, wherein the vascular graft comprises an inorganic material.

* * * * *